US007825103B2

(12) United States Patent
Nomura et al.

(10) Patent No.: US 7,825,103 B2
(45) Date of Patent: Nov. 2, 2010

(54) PYRIMIDINE NUCLEOSIDE COMPOUND OR ITS SALT

(75) Inventors: Makoto Nomura, Hanno (JP); Yayoi Ono, Hanno (JP)

(73) Assignees: Taiho Pharmaceutical Co., Ltd., Tokyo (JP); Takuma Sasaki, Nagoya-shi (JP); Akira Matsuda, Sapporo-shi (JP)

( * ) Notice: Subject to any disclaimer, the term of this patent is extended or adjusted under 35 U.S.C. 154(b) by 402 days.

(21) Appl. No.: 11/815,149

(22) PCT Filed: Jan. 30, 2006

(86) PCT No.: PCT/JP2006/301483

§ 371 (c)(1),
(2), (4) Date: Jul. 31, 2007

(87) PCT Pub. No.: WO2006/080509

PCT Pub. Date: Aug. 3, 2006

(65) Prior Publication Data
US 2009/0118222 A1 May 7, 2009

(30) Foreign Application Priority Data
Jan. 31, 2005 (JP) ............................. 2005-023278

(51) Int. Cl.
A61K 31/70 (2006.01)
C07H 19/073 (2006.01)
(52) U.S. Cl. ........................ 514/49; 536/28.5
(58) Field of Classification Search ............... None
See application file for complete search history.

(56) References Cited

U.S. PATENT DOCUMENTS 5,061,793 A 10/1991 Grindey et al.
5,691,319 A * 11/1997 Kaneko et al. ................ 514/49

FOREIGN PATENT DOCUMENTS

| JP | 61-148193 | 7/1986 |
|---|---|---|
| JP | 4 235182 | 8/1992 |
| JP | 5 194497 | 8/1993 |
| JP | 7-179491 | 7/1995 |
| JP | 2003 113197 | 4/2003 |

OTHER PUBLICATIONS

John S. Evans, et al.; "Antitumor Activity of 1-β-D-Arabinofuranosylcytosine Hydrochloride"; Pro. Soc. Exp. Bio. Med.; 1961; pp. 350-353.
Akio Hoshi, et al.; "Antitumor Activity of 1-Hexylcarbamoyl-5-Fluorouracil in a Variety of Experimental Tumors"; Oct. 1976; Gann, 67; pp. 725-731.
Kenjiro Kodama, et al.; "Antitumor Activity and Pharmacology of 1-β-D-Arabinofuranosylcytosine-5'-stearylphosphate: An Orally Active Derivative of 1-β-D-Arabinofuranosylcytosine"; Jpn. J. Cancer Res. 80, Jul. 1989; pp. 679-685.

Akira Matsuda, et al.; "Antitumor activity of sugar-modified cytosine nucleosides"; Cancer Sci; Feb. 2004; vol. 95; No. 2; pp. 105-111.
Akira Matsuda, et al.; "Protein, Nucleic Acid, and Enzyme"; 43; 1998; pp. 1981-1989 (with partial English Translation).
Matthew H. Katz, et al.; "Survival Efficacy of Adjuvant Cytosine-Analogue CS-682 in a Fluorescent Orthotopic Model of Human Pancreatic Cancer"; Cancer Research; Mar. 1, 2004; 64; pp. 1828-1833.
Akira Matsuda, et al., "Nucleosides and Nucleotides. 100. 2'-C-Cyano-2'-Deoxy-1-Beta-D-Arabinofuranosylcytosine (CNDAC): Design of a Potential Mechanism-Based DNA-Strand-Breaking Antineoplastic Nucleoside", Journal of Medicinal Chemistry, vol. 34, No. 9, pp. 2917-2919, 1991.
Atsushi Azuma, et al.,"Nucleosides and Nucleotides. 122. 2'-C-Cyano-2'-Deoxy-1-Beta-D-Arabinofuranosylcytosine and Its Derivatives. A New Class of Nucleoside With a Broad Antitumor Spectrum", Journal of Medicinal Chemistry, vol. 36, No. 26, pp. 4183-4189, 1991.

* cited by examiner

*Primary Examiner*—Lawrence E Crane
(74) *Attorney, Agent, or Firm*—Oblon, Spivak, McClelland, Maier & Neustadt, L.L.P.

(57) ABSTRACT

Provided is a pyrimidine nucleoside compound represented by the following formula (1):

(1)

or a pharmaceutically acceptable salt thereof, wherein one of X and Y represents a cyano group, and the other represents a hydrogen atom; one of $R^1$ and $R^2$ represents a hydrogen atom, a carbonyl group having a C1-C6 alkyl group which has been mono-substituted by an amino group, or a group represented by $(R^3)(R^4)(R^5)Si$—, and the other represents a group represented by $(R^6)(R^7)(R^8)Si$—, or $R^1$ and $R^2$ together form a 6-membered cyclic group represented by —$Si(R^9)(R^{10})$—; $R^3$, $R^4$, $R^5$, $R^6$, $R^7$, and $R^8$ each represent a C1-C10 linear or branched alkyl group which may have a substituent, a C3-C6 cycloalkyl group which may have a substituent, a C6-C14 aryl group which may have a substituent, or a C1-C6 alkyl group which has been substituted by one or two C6-C14 aryl groups and which may have a substituent; and $R^9$ and $R^{10}$ each represent a C1-C6 linear or branched alkyl group which may have a substituent. The pyrimidine nucleoside compound of formula (1) or a pharmaceutically acceptable salt thereof exhibits a potent antitumor effect and is therefore useful as a therapeutic agent for preventing or treating a tumor.

9 Claims, 1 Drawing Sheet

PYRIMIDINE NUCLEOSIDE COMPOUND OR ITS SALT

CROSS-REFERENCE TO RELATED APPLICATIONS

The present application is a 35 U.S.C. §371 National Stage patent application of International patent application PCT/JP2006/301483, filed on Jan. 30, 2006, which claims priority to Japanese patent application JP 2005-023278, filed on Jan. 31, 2005.

TECHNICAL FIELD

The present invention relates to a 2'-deoxy-2'-cyanopyrimidine nucleoside compound or a salt thereof which exhibits an excellent anti-tumor effect.

BACKGROUND ART

At present, cancers—characterized by anomalous cell proliferation—are diseases which are still most difficult to cure. Therefore, there is a keen demand for development of an effective drug for treating cancers. Since cell proliferation essentially involves biosynthesis of nucleic acid, hitherto, extensive studies have been carried out for developing nucleic acid metabolism antagonistic drugs which inhibit metabolism of nucleic acid.

Among these drugs, cytidine-derived nucleic acid metabolism antagonistic drugs have been developed by extensive studies. For example, cytarabine (Non-Patent Document 1), ancitabine (Non-Patent Document 2), cytarabine ocfosfate (Non-Patent Document 3), gemcitabine (Patent Document 1), etc. have been developed, and these drugs are now employed in clinical treatment.

These compounds exhibit an anti-tumor effect based on inhibition of DNA polymerase or ribonucleotide reductase, resulting in inhibition of DNA synthesis. These drugs attain clinical therapeutic results at a certain level. However, cytarabine, ancitabine, and cytarabine ocfosfate are known to have no activity to solid cancers (Non-Patent Document 4). In addition, gemcitabine can be applied to a very limited cancer type (Non-Patent Document 4). Thus, these drugs have never attained a satisfactory anti-tumor activity.

In order to solve the aforementioned problems, there has been developed 2'-cyano-2'-deoxy-1-β-D-arabinofuranosylcytosine (CNDAC) having a DNA strand breaking activity. An anti-tumor activity of CNDAC different from that of cytidine compounds which have been developed is envisaged (Patent Document 2 and Non-Patent Documents 5 and 6). In addition, 4-N-palmitoyl-2'-cyano-2'-deoxy-1-β-D-arabinofuranosylcytosine (P-CNDAC, Patent Document 3 and Non-Patent Documents 7 and 8), and 5'-phosphatidylpyrimidine nucleotide (Patent Document 4) have been developed as peroral drugs. These CNDAC compounds have been found to exhibit interesting anti-tumor effects (Non-Patent Documents 5 and 8).

However, these existing CNDAC compounds have not yet been on the market. Therefore, there is a keen demand for development and commercialization of cytidine-derived antitumor drugs exhibiting a more excellent anti-tumor effect and being perorally administrable.

[Patent Document 1] Japanese Patent Publication (kokoku) No. 6-37394
[Patent Document 2] Japanese Patent No. 2559917
[Patent Document 3] Japanese Patent No. 2569251
[Patent Document 4] Japanese Patent Application Laid-Open (kokai) No. 7-179491
[Non-Patent Document 1] Evance, J. S. et al. Proc. Soc. Exp. Bio. Med., 106, 350 (1961)
[Non-Patent Document 2] Hoshi, A. et al. Gann, 67, 725 (1972)
[Non-Patent Document 3] Kodama, K. et al. Jpn. J. Cancer Res., 80, to 685 (1989)
[Non-Patent Document 4] Matsuda, A., et al. Cancer Sci., 95, 105 to 111 (2004)
[Non-Patent Document 5] Matsuda, A., et al. J. Med. Chem., 34, 2919 to 2922 (1991)
[Non-Patent Document 6] Azuma, A., et al. J. Med. Chem., 36, 4183 to 4189 (1993)
[Non-Patent Document 7] Matsuda, Akira and Takuma, Sasaki, Protein, Nucleic Acid, and Enzyme, 43, 1981 to 1989 (1998)
[Non-Patent Document 8] Katz, M. H. et al. Cancer Res., 64, 1828 to 1833 (2004)

DISCLOSURE OF THE INVENTION

Problem to be Solved by the Invention

The present invention is directed to provision of a novel pyrimidine nucleoside compound which exhibits excellent anti-tumor effect as compared with existing pyrimidine nucleoside compounds.

Means for Carrying Out the Invention

In order to solve the problem, the present inventors have carried out extensive studies, and have found that a pyrimidine nucleoside compound represented by the following formula (1) or a salt thereof exhibits excellent bioavailability upon peroral administration and has excellent anti-tumor activity as compared with existing CNDAC compounds. The present invention has been completed based on the finding.

Accordingly, the present invention provides a novel pyrimidine nucleoside compound represented by formula (1):

[F1]

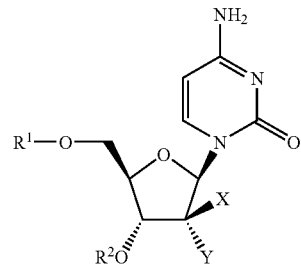

(1)

(wherein one of X and Y represents a cyano group, and the other represents a hydrogen atom; one of $R^1$ and $R^2$ represents a hydrogen atom, a carbonyl group having a C1-C6 alkyl group which has been mono-substituted by an amino group or a group represented by $(R^3)(R^4)(R^5)Si—$, and the other represents a group represented by $(R^6)(R^7)(R^8)Si—$, or $R^1$ and $R^2$ together form a 6-membered cyclic group represented by $—Si(R^9)(R^{10})—$; $R^3$, $R^4$, $R^5$, $R^6$, $R^7$, and $R^8$ each represent a C1-C10 linear or branched alkyl group which may have a substituent, a C3-C6 cycloalkyl group which may have a substituent, a C6-C14 aryl group which may have a substituent, or a C1-C6 alkyl group which has been substituted by one or two C6-C14 aryl groups and which may have a substituent; and $R^9$ and $R^{10}$ each represent a C1-C6 linear or branched alkyl group which may have a substituent) or a salt thereof.

The present invention also provides a drug composition containing an effective amount of a compound represented by formula (1) or a salt thereof and a pharmaceutically acceptable carrier.

The present invention also provides an anti-tumor agent containing an effective amount of a compound represented by formula (1) or a salt thereof and a pharmaceutically acceptable carrier.

The present invention also provides use of a compound represented by formula (1) or a salt thereof for production of a drug.

The present invention also provides a method for treating a tumor, comprising administering an effective amount of a compound represented by formula (1) or a salt thereof.

EFFECTS OF THE INVENTION

The novel pyrimidine nucleoside compound of the present invention and salts thereof have excellent anti-tumor activity and good absorbability upon peroral administration, and thus are useful as an anti-tumor agent.

BEST MODE FOR CARRYING OUT THE INVENTION

Figure 1:
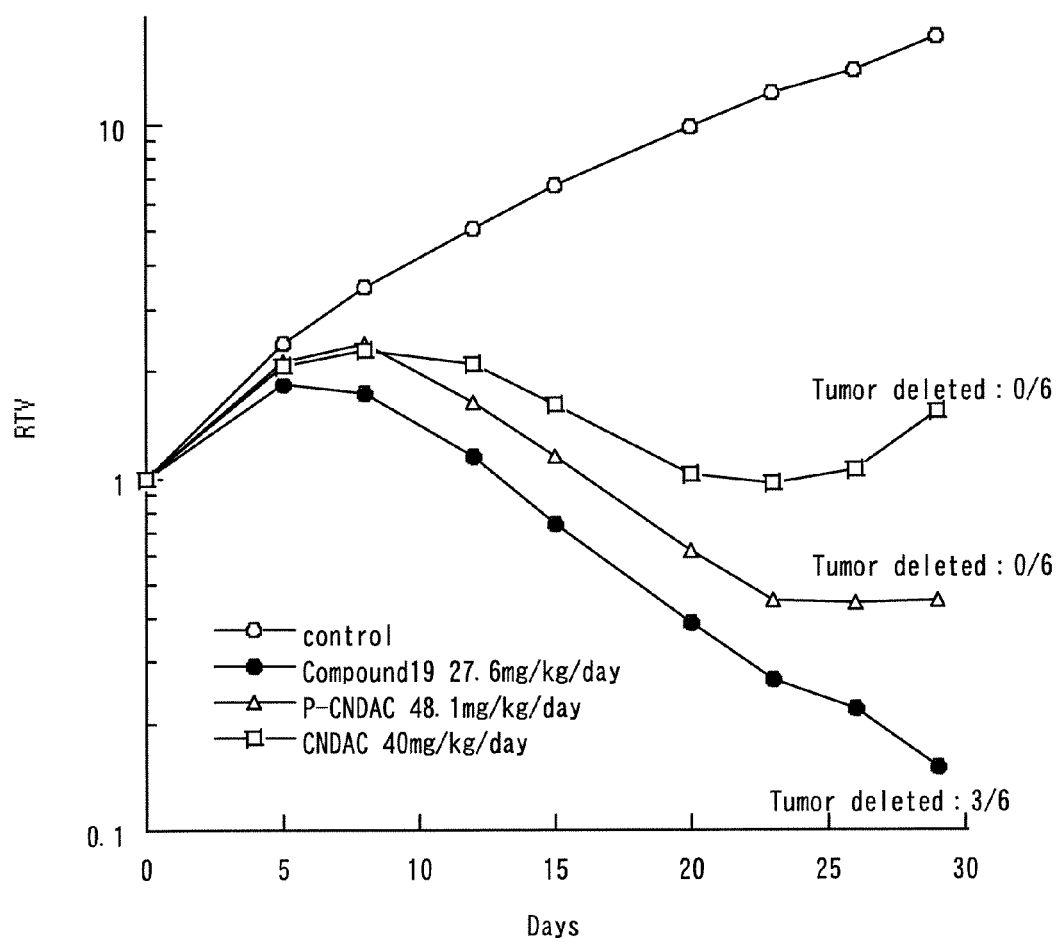
FIG. 1 shows a graph showing change in tumor volume when an equitoxic amount of Compound 19, CNDAC, or P-CNDAC is used against human large intestine cancer cell strain KM20C.

The novel pyrimidine nucleoside compound of the present invention and salts thereof have a chemical structure which is represented by the above formula (1) and which is characterized by having silyl groups at the 3'- and 5'-positions.

Some intermediate compounds for synthesis of the above CNDAC compounds are known to have silyl groups at 3'- and 5'-positions thereof (for example, Patent Documents 2 and 3). However, the CNDAC compound of the present invention represented by formula (1) has not been disclosed. In addition, the anti-tumor activity of the intermediate compounds for synthesis of the above CNDAC compounds has not been known.

In formula (1), examples of the "C1-C6 alkyl group" of the "a carbonyl group having a C1-C6 alkyl group which has been mono-substituted by an amino group" represented by $R^1$ or $R^2$ include methyl, ethyl, propyl, isopropyl, butyl, isobutyl, tert-butyl, n-pentyl, and n-hexyl, with isobutyl being preferred.

In formula (1), examples of the "C1-C10 linear or branched alkyl group" represented by $R^3$, $R^4$, $R^5$, $R^6$, $R^7$, or $R^8$ include methyl, ethyl, n-propyl, isopropyl, n-butyl, tert-butyl, n-hexyl, n-octyl, and thexyl. Preferably, the "C1-C10 linear or branched alkyl group" is a C1-C8 linear or branched alkyl group. More preferably, any one of $R^3$, $R^4$, and $R^5$ and any one of $R^6$, $R^7$, and $R^8$, in which the selected ones may be identical to or different from each other, are each a C3-C8 linear or branched alkyl group, and the other groups, which may be identical to or different from one another, are each a C1-C4 linear or branched alkyl group.

In formula (1), examples of the "C3-C6 cycloalkyl group" represented by $R^3$, $R^4$, $R^5$, $R^6$, $R^7$ or $R^8$ include cyclopropyl, cyclobutyl, cyclopentyl, and cyclohexyl. Among them, cyclopropyl and cyclohexyl are preferred, and cyclopropyl is more preferred.

In formula (1), examples of the "C6-C14 aryl group" represented by $R^3$, $R^4$, $R^5$, $R^6$, $R^7$, or $R^8$ include phenyl and naphthyl.

In formula (1), the "C6-C14 aryl group" of the "C1-C6 alkyl group which has been substituted by one or two C6-C14 aryl groups" represented by $R^3$, $R^4$, $R^5$, $R^6$, $R^7$, or $R^8$ is a group corresponding to the above C6-C14 aryl group, and the "C1-C6 alkyl group" is a group corresponding to the above C1-C6 alkyl group. Specific examples include benzyl, phenethyl, benzhydryl, and naphthylmethyl.

In formula (1), the "substituent" which may be bonded to $R^3$, $R^4$, $R^5$, $R^6$, $R7^7$, $R^8$, $R^9$, or $R^{10}$ may be identical to or different from one another (number of substitution(s): one to three). The substituent is selected from the group consisting of a C1-C3 linear or branched alkyl group; a hydroxyl group; a C1-C6 linear or branched alkoxy group; an amino group; a halogen atom; a cyano group; and a nitro group.

In formula (1), examples of the "$(R^3)(R^4)(R^5)Si$—" and "$(R^6)(R^7)(R^8)Si$—" represented by $R^1$ and $R^2$ include tert-butyldimethylsilyl, triisopropylsilyl, triisobutylsilyl, dimethyl-n-octylsilyl, dimethylthexylsilyl, trimethylsilyl, triethylsilyl, tri-n-propylsilyl, tri-n-butylsilyl, tri-n-hexylsilyl, n-propyldimethylsilyl, n-butyldimethylsilyl, isobutyldimethylsilyl, n-pentyldimethylsilyl, n-hexyldimethylsilyl, dimethyl-tert-hexylsilyl, n-decyldimethylsilyl, (3,3-dimethylbutyl)dimethylsilyl, 2,3-dimethylpropyldimethylsilyl, di-tert-butylmethylsilyl, di-n-butylmethylsilyl, diethylisopropylsilyl, n-octyldiisopropylsilyl, n-octyldiisobutylsilyl, cyclohexyldimethylsilyl, dicyclohexylmethylsilyl, isopropyldiphenylsilyl, triphenylsilyl, dimethylphenylsilyl, tert-butyldiphenylsilyl, methyldiphenylsilyl, diphenyl (diphenylmethyl)silyl, p-tolyldimethylsilyl, biphenyldimethylsilyl, m-phenoxyphenyldimethylsilyl, biphenyldiisopropylsilyl, tri(2-biphenyl)silyl, tri(o-tolyl)silyl, tri(2-methoxyphenyl)silyl, tribenzylsilyl, benzyldimethylsilyl, phenethyldimethylsilyl, (3-phenylpropyl)dimethylsilyl, p-(tert-butyl)phenethyldimethylsilyl, phenethyldiisopropylsilyl, neophyldimethylsilyl, bromomethyldimethylsilyl, chloromethyldimethylsilyl, 4-chlorobutyldimethylsilyl, (dichloromethyl)dimethylsilyl, 3-chloropropyldimethylsilyl, 3,3,3-trifluoropropyldimethylsilyl, 1H,1H,2H,2H-perfluoro-n-decyldimethylsilyl, 1H,1H,2H,2H-perfluoro-n-octyldimethylsilyl, 3,3,4,4,5,5,6,6,6-nonafluoro-n-hexyldimethylsilyl, bis(chloromethyl)methylsilyl, pentafluorophenyldimethylsilyl, pentafluorophenylpropyldimethylsilyl, 3,5-bis(trifluoromethyl)phenyldimethylsilyl, [3-(chloromethyl)phenylethyl]dimethylsilyl, [4-(chloromethyl)phenylethyl]dimethylsilyl, acetoxyethyldimethylsilyl, 3-acetoxypropyldimethylsilyl, 3-methacryloxypropyldimethylsilyl, 3-cyanopropyldiisopropylsilyl, [3-(trimethylsiloxy)propyl]dimethylsilyl, n-butyldiisopropylsilyl, diisopropyl-n-propylsilyl, diisopropyl (2,2-dimethylpropyl)silyl, (3-methylbutyl)diisopropylsilyl, (2-ethylbutyl)dicyclopropylsilyl, tert-amyldiethylsilyl, tert-butyldiisobutylsilyl, diethyl(3-methylpentan-3-yl)silyl, isobutyldiisopropylsilyl, diethyl(2-methylpentan-2-yl)silyl, cyclopropyldiisopropylsilyl, dicyclopropylisobutylsilyl, diisopropyl(3-methoxypropyl)silyl, (3-ethoxypropyl)diisopropylsilyl, [3-(tert-butyloxy)propyl]diisopropylsilyl, tert-butyldi(3-ethoxypropyl) silyl, and 3-phenoxypropyldimethylsilyl. Preferably, the "$(R^3)(R^4)(R^5)Si$—" and "$(R^6)(R^7)(R^8)Si$—" are each tert-butyldimethylsilyl, triisopropylsilyl, diethylisopropylsilyl, cyclohexyldimethylsilyl, triisobutylsilyl, triphenylsilyl, tribenzylsilyl, dimethylphenylsilyl, dimethyl-n-octylsilyl, dicyclopropyl(2-ethylbutyl)silyl, diethyl(3-methylpentan-3-yl)silyl, tert-butyldiisobutylsilyl, cyclopropyldiisopropylsilyl, or dimethylthexylsilyl, more preferably tert-butyldimethylsilyl, triisopropylsilyl, diethylisopropylsilyl, dimethyl-n-octylsilyl, cyclopropyldiisopropylsilyl, or dimethylthexylsilyl, particularly preferably triisopropylsilyl, cyclopropyldiisopropylsilyl, or dimethylthexylsilyl.

In formula (1), the "C1-C6 linear or branched alkyl group" represented by $R^9$ or $R^{10}$ include methyl, ethyl, n-propyl, isopropyl, n-butyl, tert-butyl, and n-hexyl.

<Preferred Pyrimidine Nucleoside Compound>

The compound of the present invention is preferably a compound represented by formula (1), wherein one of X and Y represents a cyano group, and the other represents a hydrogen atom; one of $R^1$ and $R^2$ represents a hydrogen atom, a group represented by $(R^3)(R^4)(R^5)Si$— or a carbonyl group having a C1-C6 alkyl group which has been mono-substituted by an amino group and the other represents a group represented by $(R^6)(R^7)(R^8)Si$—, or $R^1$ and $R^2$ together form a 6-membered cyclic group represented by —$Si(R^9)(R^{10})$—; $R^3$, $R^4$, $R^5$, $R^6$, $R^7$, and $R^8$, which may be identical to or different from one another, individually represent a C3-C6 cycloalkyl group, a phenyl group, a benzyl group, or a C1-C8 linear or branched alkyl group which may have a C1-C6 alkoxy group.

The compound of the present invention is more preferably a compound represented by formula (1), wherein one of X and Y represents a cyano group, and the other represents a hydrogen atom; $R^1$ represents a hydrogen atom, a valyl group, or a group represented by $(R^3)(R^4)(R^5)Si$—; $R^2$ represents a hydrogen atom or a group represented by $(R^6)(R^7)(R^8)Si$— (in the case where $R^1$ is a hydrogen atom or a valyl group, $R^2$ does not represent a hydrogen atom); and $R^3$, $R^4$, $R^5$, $R^6$, $R^7$, and $R^8$, which may be identical to or different from one another, each represent a C1-C8 linear or branched alkyl group or a C3-C6 cycloalkyl group.

The compound of the present invention is still more preferably a compound represented by formula (1), wherein one of X and Y represents a cyano group, and the other represents a hydrogen atom; $R^1$ represents a hydrogen atom, an L-valyl group, or a group represented by $(R^3)(R^4)(R^5)Si$—; $R^2$ represents a hydrogen atom or a group represented by $(R^6)(R^7)(R^8)Si$— (in the case where $R^1$ represents a hydrogen atom or an L-valyl group, $R^2$ does not represent a hydrogen atom); and any one of $R^3$, $R^4$, and $R^5$ and any one of $R^6$, $R^7$, and $R^8$, in which the selected ones may be identical to or different from each other, individually represent a C3-C8 linear or branched alkyl group or a cyclopropyl group, and the other groups, which may be identical to or different from each other, each represent a C1-C4 linear or branched alkyl group.

The compound of the present invention is particularly more preferably a compound represented by formula (1), wherein one of X and Y represents a cyano group, and the other represents a hydrogen atom; $R^1$ represents a hydrogen atom, an L-valyl group, a triisopropylsilyl group, a diethylisopropylsilyl group, a dimethylthexylsilyl group, or a dimethyl-n-octylsilyl group; $R^2$ represents a hydrogen atom, a tert-butyldimethylsilyl group, a triisopropylsilyl group, a diethylisopropylsilyl group, a cyclopropyldiisopropylsilyl group, or a dimethylthexylsilyl group (in the case where $R^1$ represents a hydrogen atom or an L-valyl group, $R^2$ does not represent a hydrogen atom).

Preferred examples of the pyrimidine nucleoside compound include the following (a) to (k):

(a) 5'-O-triisopropylsilyl-2'-cyano-2'-deoxy-1-β-D-arabinofuranosylcytosine;
(b) 5'-O-diethylisopropylsilyl-2'-cyano-2'-deoxy-1-β-D-arabinofuranosylcytosine;
(c) 5'-O-dimethylthexylsilyl-2'-cyano-2'-deoxy-1-β-D-arabinofuranosylcytosine;
(d) 5'-O-(dimethyl-n-octylsilyl)-2'-cyano-2'-deoxy-1-β-D-arabinofuranosylcytosine;
(e) 3'-O-dimethylthexylsilyl-2'-cyano-2'-deoxy-1-β-D-arabinofuranosylcytosine;
(f) 3'-O-diethylisopropylsilyl-2'-cyano-2'-deoxy-1-β-D-arabinofuranosylcytosine;
(g) 3'-O-(tert-butyldimethylsilyl)-2'-cyano-2'-deoxy-1-β-D-arabinofuranosylcytosine;
(h) 3'-O-triisopropylsilyl-2'-cyano-2'-deoxy-1-β-D-arabinofuranosylcytosine;
(i) 3'-O-dimethylthexylsilyl-5'-O-(L-valyl)-2'-cyano-2'-deoxy-1-β-D-arabinofuranosylcytosine;
(j) 5'-O-(L-valyl)-3'-O-(tert-butyldimethylsilyl)-2'-cyano-2'-deoxy-1-β-D-arabinofuranosylcytosine; and
(k) 3'-O-cyclopropyldiisopropylsilyl-2'-cyano-2'-deoxy-1-β-D-arabinofuranosylcytosine.

No particular limitation is imposed on the salt of the pyrimidine nucleoside compound of the present invention, so long as the salt is pharmacologically acceptable. Examples of the salt which may be formed include mineral acid salts such as hydrochloride, hydrobromide, sulfate, nitrate, and phosphate; and organic acid salts such as acetate, propionate, tartrate, fumarate, maleate, malate, citrate, methanesulfonate, p-toluenesulfonate, and trifluoroacetate. Depending on the type of the substituent(s), the pyrimidine nucleoside compound of the present invention may form optical isomers or geometrical isomers. The pyrimidine nucleoside compound of the present invention encompasses such optical isomers and geometrical isomers. These isomers may be resolved or used as a mixture. The pyrimidine nucleoside compound of the present invention also encompasses amorphous species, polymorphisms, and solvates such as hydrates.

The pyrimidine nucleoside compound of the present invention or a salt thereof may be produced in accordance with the following reaction scheme including Steps 1 to 11.

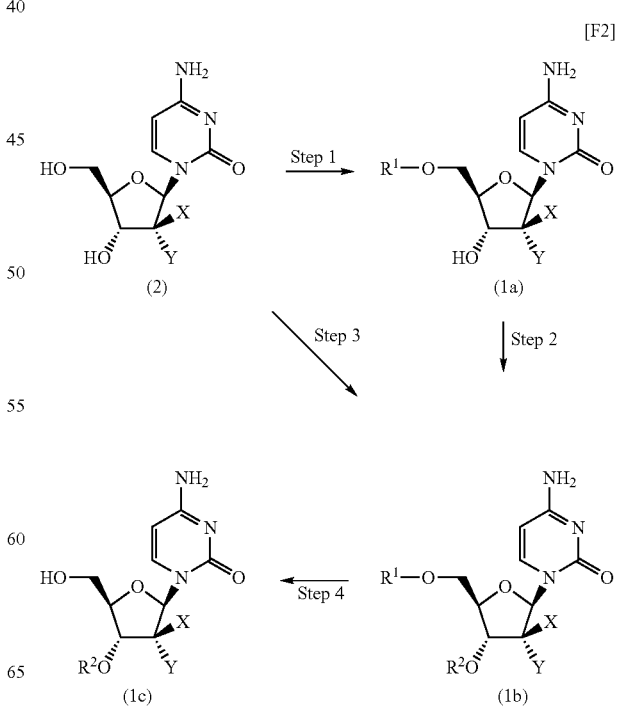

[F2]

-continued

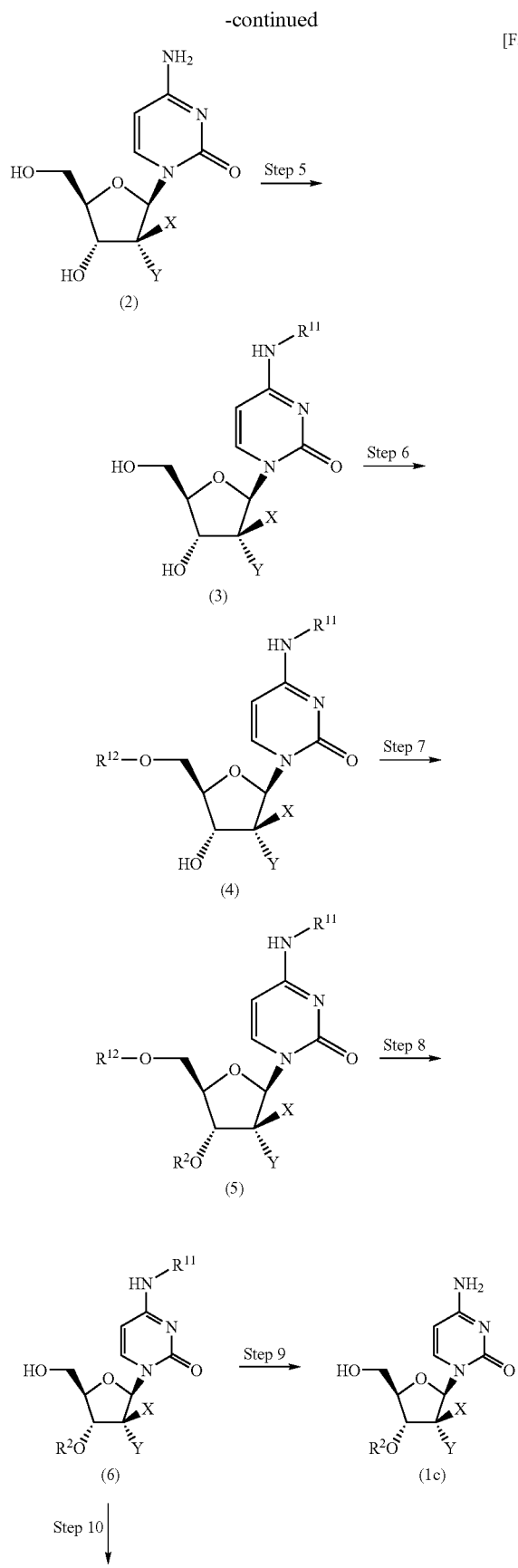

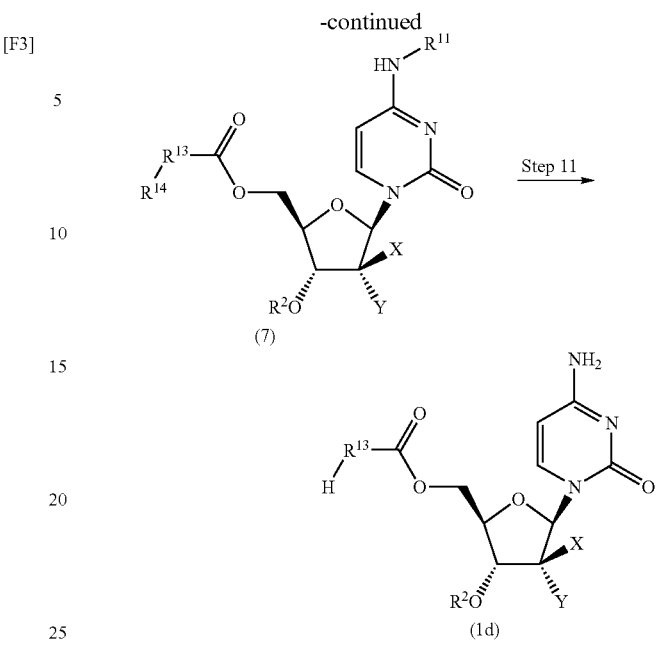

X, Y, $R^1$, and $R^2$ shown in Steps 1 to 11 have the same meanings as described above. Each of $R^{11}$ and $R^{14}$ represents a protective group with respect to the amino group. No particular limitation is imposed on the protective group, and any conventionally known protective group may be employed. For example, appropriate protective groups include those recited in the document (T. W. Greene, "Protective groups in Organic Synthesis", A Wiley-Interscience Publication, John-Wiley & Sons, New York, 1981, p. 218-287). Specific examples include substituted oxycarbonyl groups such as a tert-butoxycarbonyl group and a benzyloxycarbonyl group. $R^{12}$ is a protective group with respect to the hydroxyl group, and examples include a triphenylmethyl group, a 4-methoxytriphenylmethyl group, and a 4,4'-dimethoxytriphenylmethyl group. The moiety $R^{13}$—$CO_2H$ represents an amino-mono-substituted carboxylic acid, and examples include amino acids such as glycine, L-alanine, β-alanine, L-valine, L-leucine, L-isoleucine, L-lysine, and D-alanine.

(Step 1)

In Step 1, a pyrimidine nucleoside compound represented by formula (2) or a salt thereof is reacted with a generally known silylating agent such as trialkylsilyl halide, trialkylsilyl triflate, or trialkylsilylacetamide represented by $(R^3)(R^4)(R^5)Si$—Z or $(R^6)(R^7)(R^8)Si$—Z (wherein Z represents a halogen atom, a trifluoromethanesulfonyloxy group, an acetamino group, etc.), whereby a compound represented by formula (1a) can be produced. The reaction may be carried out in accordance with any known method. No particular limitation is imposed on the solvent employed in the reaction, so long as the solvent is inert to the reaction. Examples of the solvent include dichloromethane, chloroform, ethyl acetate, tetrahydrofuran, dioxane, diethyl ether, benzene, toluene, N,N-dimethylformamide, and dimethyl sulfoxide. These solvents may be used singly or in combination. In the reaction, a base may further be used in accordance with needs. Examples of the base include organic amines such as imidazole, 1-methylimidazole, trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogencarbonate, sodium carbonate, and potassium carbonate. The solvent may be formed sole from a base. In the reaction, the aforementioned $(R^3)(R^4)(R^5)Si$—Z or $(R^6)(R^7)(R^8)Si$—Z is used in an amount of about 1 to 10 mol, preferably about 1 to 5 mol, and a base is used in an amount of about 1 to 100 mol, preferably about 1 to 10 mol, with respect to 1 mol of the compound represented by formula (2). Temperature and time of the reaction are −30 to 100° C. and 0.1 to 100 hours, preferably 0 to 30° C. and 1 to 20 hours. The compound represented by formula (1a) and produced through the reaction may be isolated and purified in accordance with needs. Alternatively, the as-produced compound may also be used in a subsequent step without further purification. The trialkylsilyl halide employed in the reaction and represented by $(R^3)(R^4)(R^5)$ Si—Z or $(R^6)(R^7)(R^8)$ Si—Z may be prepared through a known method. For example, trihalogenosilane, monoalkyldihalogenosilane, or dialkylmonohalogenosilane is reacted with a corresponding alkyllithium or Grignard reagent, to thereby form a trialkylsilane represented by $(R^3)(R^4)(R^5)Si$—H or $(R^6)(R^7)(R^8)Si$—H, and the product is further reacted with a halogen species such as N-chlorosuccinimide, N-bromosuccinimide, N-iodosuccinimide, chlorine, bromine, iodine, or 1,3-dichloro-5,5-dimethylhydantoin, to thereby produce a trialkylsilyl halide. During production of the trialkylsilane represented by $(R^3)(R^4)(R^5)Si$—H, an additive such as copper bromide may be used. The trialkylsilane represented by $(R^3)(R^4)(R^5)Si$—H or $(R^6)(R^7)(R^8)Si$—H and the trialkylsilyl halide represented by $(R^3)(R^4)(R^5)Si$—Z or $(R^6)(R^7)(R^8)Si$—Z may be isolated and purified in accordance with needs. Alternatively, the as-produced compounds may also be used in Step 1.

(Step 2)

In Step 2, the pyrimidine nucleoside compound represented by formula (1a) is reacted with the aforementioned $(R^3)(R^4)(R^5)Si$—Z or $(R^6)(R^7)(R^8)Si$—Z in the presence of a base, whereby a compound represented by formula (1b) is produced. Step 2 is performed in a manner similar to that of Step 1.

(Step 3)

In Step 3, the pyrimidine nucleoside compound represented by formula (2) is reacted with the aforementioned $(R^3)(R^4)(R^5)Si$—Z or $(R^6)(R^7)(R^8)Si$—Z or with a compound such as dialkylsilyl dihalide or dialkylsilyl ditriflate represented by Z—$Si(R^9)(R^{10})$—Z (wherein Z has the same meaning as mentioned above), in the presence of a base, whereby a compound represented by formula (1b) can be produced in a manner similar to that of Step 1. Temperature and time of the reaction are −30 to 150° C. and 0.1 to 100 hours, preferably 0 to 100° C. and 1 to 40 hours. The compound represented by formula (1b) and produced through the reaction may be isolated and purified in accordance with needs. Alternatively, the as-produced compound may also be used in a subsequent step without further purification.

(Step 4)

In Step 4, the pyrimidine nucleoside compound represented by formula (1b) is treated under acidic conditions, to thereby produce a compound represented by formula (1c). No particular limitation is imposed on the acid employed in Step 4, so long as the acid enables to remove a substituent represented by $R^1$. Examples of the acid include mineral acids such as hydrochloric acid, hydrobromic acid, sulfuric acid, nitric acid, and phosphoric acid; and organic acids such as trifluoroacetic acid, acetic acid, propionic acid, formic acid, methanesulfonic acid, and p-toluenesulfonic acid. These acids may be mixed with water, and a solvent may further be used in accordance with needs. Examples of the solvent to be used include dichloromethane, chloroform, ethyl acetate, tetrahydrofuran, dioxane, diethyl ether, benzene, toluene, N,N-dimethylformamide, dimethyl sulfoxide, methanol, ethanol, n-propanol, isopropanol, and water. These solvents may be used singly or in combination. Temperature and time of the reaction are −30 to 150° C. and 0.1 to 100 hours, preferably 0 to 100° C. and 1 to 20 hours.

(Step 5)

In Step 5, the pyrimidine nucleoside compound represented by formula (2) is reacted with an amino group-protecting reagent, to thereby produce a compound represented by formula (3). No particular limitation is imposed on the solvent employed in the reaction, so long as the solvent is inert to the reaction. Examples of the solvent include dichloromethane, chloroform, ethyl acetate, tetrahydrofuran, dioxane, diethyl ether, benzene, toluene, N,N-dimethylformamide, and dimethyl sulfoxide. These solvents may be used singly or in combination. In the reaction, a base may further be used in accordance with needs. Examples of the base include organic amines such as imidazole, 1-methylimidazole, trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogencarbonate, sodium carbonate, and potassium carbonate. The solvent may be formed sole from a base. No particular limitation is imposed on the amino group-protecting reagent to be employed, so long as the protective group can be removed under acidic or neutral conditions, and examples include alkoxycarbonyl halides such as tert-butoxycarbonyl chloride; alkyl carbonate anhydrides such as di-tert-butyldicarbonate; and aralkyloxycarbonyl halides such as benzyloxycarbonyl chloride. Temperature and time of the reaction are −30 to 150° C. and 0.1 to 100 hours, preferably 0 to 100° C. and 1 to 40 hours. The compound represented by formula (3) and produced through the reaction may be isolated and purified in accordance with needs. Alternatively, the as-produced compound may also be used in a subsequent step without further purification.

(Step 6)

In Step 6, the pyrimidine nucleoside compound represented by formula (3) is reacted with a hydroxyl group-protecting reagent in the presence of a base, to thereby produce a compound represented by formula (4). Examples of the base include organic amines such as imidazole, 1-methylimidazole, trimethylamine, triethylamine, tripropylamine, diisopropylethylamine, N-methylmorpholine, pyridine, lutidine, and collidine; and inorganic bases such as sodium hydrogencarbonate, sodium carbonate, and potassium carbonate. The solvent may be formed sole from a base. No particular limitation is imposed on the solvent employed in the reaction, so long as the solvent is inert to the reaction. Examples of the solvent include dichloromethane, chloroform, ethyl acetate, tetrahydrofuran, dioxane, diethyl ether, benzene, toluene, N,N-dimethylformamide, and dimethyl sulfoxide. These solvents may be used singly or in combination. No particular limitation is imposed on the hydroxyl group-protecting reagent to be employed, so long as the protective group can selectively protect the 5'-hydroxyl group in a sugar moiety and can be removed under acidic or neutral conditions, and examples include triarylmethyl halides such as triphenylmethyl chloride, 4-methoxytriphenylmethyl chloride, and 4,4-dimethoxytriphenylmethyl chloride. Temperature and time of the reaction are −30 to 150° C. and 0.1 to 100 hours, preferably 0 to 100° C. and 1 to 40 hours. The compound represented by formula (4) and produced through the reaction may be isolated and purified in accordance with needs. Alternatively, the as-produced compound may also be used in a subsequent step without further purification.

(Step 7)

In Step 7, the pyrimidine nucleoside compound represented by formula (4) is reacted with the aforementioned $(R^3)(R^4)(R^5)Si$—Z or $(R^6)(R^7)(R^8)Si$—Z in the presence of a base, to thereby produce a compound represented by formula (5). Examples of the base include organic amines such as imidazole, 1-methylimidazole, trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogencarbonate, sodium carbonate, and potassium carbonate. The solvent may be formed sole from a base. No particular limitation is imposed on the solvent employed in the reaction, so long as the solvent is inert to the reaction. Examples of the solvent include dichloromethane, chloroform, ethyl acetate, tetrahydrofuran, dioxane, diethyl ether, benzene, toluene, N,N-dimethylformamide, and dimethyl sulfoxide. These solvents may be used singly or in combination. The compound represented by formula (5) and produced through the reaction may be isolated and purified in accordance with needs. Alternatively, the as-produced compound may also be used in a subsequent step without further purification.

(Step 8)

In Step 8, the pyrimidine nucleoside compound represented by formula (5) is reacted with a deprotecting reagent, to thereby produce a compound represented by formula (6). In the case where the protective group for the 5'-hydroxyl group in a sugar moiety is a triarylmethyl group, examples of the solvent to be employed include dichloromethane, chloroform, ethyl acetate, tetrahydrofuran, dioxane, diethyl ether, benzene, toluene, acetone, N,N-dimethylformamide, dimethyl sulfoxide, methanol, ethanol, n-propanol, isopropanol, and water. These solvents may be used singly or in combination. No particular limitation is imposed on the deprotecting reagent to be employed, and those conventionally employed may be chosen. For example, in the case where the protective group for the 5'-hydroxyl group in a sugar moiety is a triarylmethyl group, examples of the deprotecting reagent include mineral acids such as hydrochloric acid, hydrobromic acid salts, sulfuric acid, nitric acid, and phosphoric acid; and organic acids such as trifluoroacetic acid, acetic acid, propionic acid, formic acid, methanesulfonic acid, and p-toluenesulfonic acid. Temperature and time of the reaction are –30 to 150° C. and 0.1 to 100 hours, preferably 0 to 100° C. and 1 to 40 hours. The compound represented by formula (6) and produced through the reaction may be isolated and purified in accordance with needs. Alternatively, the as-produced compound may also be used in a subsequent step without further purification.

(Step 9)

In Step 9, the pyrimidine nucleoside compound represented by formula (6) is reacted with a deprotecting reagent, to thereby produce a compound represented by formula (1c). In the case where the protective group for the 4-amino group is a tert-butoxycarbonyl group, examples of the solvent to be employed include dichloromethane, chloroform, ethyl acetate, tetrahydrofuran, dioxane, diethyl ether, benzene, toluene, acetone, N,N-dimethylformamide, dimethyl sulfoxide, methanol, ethanol, n-propanol, isopropanol, and water. These solvents may be used singly or in combination. No particular limitation is imposed on the deprotecting reagent, and those conventionally employed may be chosen. For example, in the case where the protective group for the 4-amino group is a tert-butoxycarbonyl group, examples of the deprotecting reagent include mineral acids such as hydrochloric acid, hydrobromic acid, sulfuric acid, nitric acid, and phosphoric acid; and organic acids such as trifluoroacetic acid, acetic acid, propionic acid, formic acid, methanesulfonic acid, and p-toluenesulfonic acid. Temperature and time of the reaction are –30 to 150° C. and 0.1 to 100 hours, preferably 0 to 100° C. and 1 to 40 hours. Note that Steps 8 and 9 may be performed as one single step instead of two separate steps.

(Step 10)

In Step 10, the pyrimidine nucleoside compound represented by formula (6) is condensed with a corresponding amino-group-protected carboxylic acid, to thereby produce a carboxylic acid ester represented by formula (7). No particular limitation is imposed on the mode of condensation reaction, so long as the condensation is performed between conventional carboxylic acid and alcohol for forming an ester. For example, an acid anhydride mixture, a condensing agent, etc. may be employed. When an acid anhydride mixture is employed, examples of the base include organic amines such as trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogencarbonate, sodium carbonate, and potassium carbonate. Examples of the reagent employed for forming an acid anhydride mixture with an amino-group-protected amino acid include isobutyl chlorocarbonate and pivaloyl chloride. Examples of the condensing agent include carbodiimide compounds such as dicyclohexylcarbodiimide and 1-ethyl-3-(3-dimethylaminopropyl)carbodiimide hydrochloride, and N,N'-carbonyldiimidazole. Examples of the condensing aid include 1-hydroxybenzotriazole hydrate, N-hydroxysuccinimide, N-hydroxy-5-norbornene-2,3-dicarboximide, and 4-dimethylaminopyridine. No particular limitation is imposed on the solvent employed in the reaction, so long as the solvent is inert to the reaction. Examples of the solvent include dichloromethane, chloroform, ethyl acetate, tetrahydrofuran, dioxane, diethyl ether, benzene, toluene, N,N-dimethylformamide, and dimethyl sulfoxide. These solvents may be used singly or in combination. The compound represented by formula (7) and produced through the reaction may be isolated and purified in accordance with needs. Alternatively, the as-produced compound may also be used in a subsequent step without further purification.

(Step 11)

In Step 11, the pyrimidine nucleoside compound represented by formula (7) is reacted with a deprotecting reagent, to thereby produce a compound represented by formula (1d). In the case where each of the protective groups for the 5'-amino and 4-amino groups is a tert-butoxycarbonyl group, examples of the solvent to be employed include dichloromethane, chloroform, ethyl acetate, tetrahydrofuran, dioxane, diethyl ether, benzene, toluene, acetone, N,N-dimethylformamide, dimethyl sulfoxide, methanol, ethanol, n-propanol, isopropanol, and water. These solvents may be used singly or in combination. No particular limitation is imposed on the deprotecting reagent, and those conventionally employed may be chosen. For example, in the case where each of the protective groups for these amino groups is a tert-butoxycarbonyl group, examples of the deprotecting reagent include mineral acids such as hydrochloric acid, hydrobromic acid, sulfuric acid, nitric acid, and phosphoric acid; and organic acids such as trifluoroacetic acid, acetic acid, propionic acid, formic acid, methanesulfonic acid, and p-toluenesulfonic acid. Temperature and time of the reaction are −30 to 150° C. and 0.1 to 100 hours, preferably 0 to 100° C. and 1 to 40 hours.

The thus-produced compound of the present invention and other compounds may be transformed into salts thereof, particularly pharmaceutically acceptable salts, through a generally known method.

The compound of the present invention, a salt thereof, other compounds, and salts thereof may be isolated and purified through a generally known separation/purification method such as concentration, solvent extraction, filtration, recrystallization, or any chromatographic technique.

Upon use of the compound of present invention as a drug, the compound is blended with a pharmaceutical carrier, and a variety of administration forms may be chosen in accordance with prophylactic and treatment purposes. Any administration forms may be employed, and examples include peroral drugs, injections, suppositories, ointments, and patches. Of these, peroral forms are preferably employed. These drug forms may be produced through any pharmaceutical techniques known in the art.

The pharmaceutical carrier to be employed may be any organic and inorganic carrier substances which are customarily employed as materials for drug preparation. In solid drugs, the carrier is incorporated in the form of a vehicle, a lubricant, a binder, a disintegrant, or a similar additive. In liquid drugs, the carrier is incorporated as a solvent, a dissolution aid, a suspending agent, a tonicity agent, a buffer, a soothing agent, or a similar additive. Other additives such as a preservative, an antioxidant, a colorant, and a sweetening agent may also be incorporated in accordance with needs.

In preparation of a peroral solid drug, the compound of the present invention is blended with a vehicle and optional additives such as a binder, a disintegrant, a lubricant, a colorant, and a sweetening/flavoring agent, and the mixture is formed into tablets, coated tablets, granules, powder, capsules, etc. through a routine method. These additives may be those generally employed in the art, and examples include lactose, sucrose, sodium chloride, glucose, starch, calcium carbonate, kaolin, microcrystalline cellulose, and silicic acid (vehicles); water, ethanol, propanol, simple syrup, glucose liquid, starch liquid, gelatin liquid, carboxymethylcellulose, hydroxypropylcellulose, hydroxypropylstarch, methylcellulose, ethylcellulose, shellac, calcium phosphate, and polyvinylpyrrolidone (binders); dry starch, sodium alginate, agar powder, sodium hydrogencarbonate, calcium carbonate, sodium lauryl sulfate, stearic acid monoglyceride, and lactose (disintegrants); purified talc, stearic acid salts, borax, and polyethylene glycol (lubricants); titanium oxide and iron oxide (colorants); and sucrose, orange peel, citric acid, and tartaric acid (sweetening/flavoring agents).

In preparation of a peroral liquid drug, the compound of the present invention is blended with additives such as a sweetening agent, a buffer, a stabilizer, and a flavoring agent, and the mixture is formed into a peroral liquid drug, a syrup, an elixir, etc., through a routine method. In this case, the sweetening/flavoring agent may be the same as described above. Examples of the buffer include sodium citrate, and examples of the stabilizer include tragacanth, acacia, and gelatin.

In preparation of an injection, the compound of the present invention is blended with additives such as a pH-regulator, a buffer, a stabilizer, a tonicity agents, and a local anesthetic, and the mixture is formed into subcutaneous, intramuscular, and intravenous injections, through a routine method. In this case, examples of the pH-regulator and the buffer include sodium citrate, sodium acetate, and sodium phosphate, and examples of the stabilizer include sodium pyrosulfite, EDTA, thioglycolic acid, and thiolactic acid. Examples of the local anesthetic include procaine hydrochloride and lidocaine hydrochloride. Examples of the tonicity agent include sodium chloride and glucose.

In preparation of a suppository drug, the compound of the present invention is blended with a carrier for drug preparation known in the art, such as polyethylene glycol, lanolin, cacao butter, and fatty acid triglyceride and an optional surfactant such as Tween (registered trademark), and the mixture is formed into suppositories through a routine method.

In preparation of an ointment, the compound of the present invention is blended, in accordance with needs, with generally employed additives such as a base, a stabilizer, a moisturizer, a preservative, etc., and the mixture is mixed and formed into a drug through a routine method. Examples of the ointment base include liquid paraffin, white vaseline, white beeswax, octyl dodecyl alcohol, and paraffin. Examples of the preservative include p-oxymethyl benzoate, p-oxyethyl benzoate, and p-oxypropyl benzoate.

In preparation of a patch drug, the aforementioned ointment, cream, gel, paste, or a similar material is applied to a customary support through a routine method. Examples of suitable supports include woven and non-woven fabric of cotton, staple fiber, or chemical fiber; and films and foamed sheet made of soft vinyl chloride, polyethylene, or polyurethane.

The unit dose of the compound of the present invention which is to be incorporated in any of the aforementioned drugs varies in accordance with the condition of the patients to whom the compound of the invention is to be administered, the form of drugs, or other factors. Generally, the unit dose is preferably about 0.05 to 1,000 mg for peroral drugs, about 0.01 to 500 mg for injections, and about 1 to 1,000 mg for suppositories. The daily dose of a drug containing any of the aforementioned drug forms, which varies depending on the condition, body weight, age, sex, etc, of the patient, cannot consistently be determined. However, generally, the daily dose per adult is about 0.05 to 5,000 mg, preferably 0.1 to 1,000 mg. The unit dose is preferably administered one per day or in a divided manner of twice to four times.

Examples of the diseases (in the case of malignant tumors) which can be cured through administration of a drug containing the compound of the present invention include head and neck cancer, esophageal cancer, gastric cancer, colonic cancer, rectum cancer, liver cancer, gallbladder/bile duct cancer, pancreatic cancer, lung cancer, mammary cancer, ovarian cancer, cervical cancer, uterine corpus cancer, renal cancer, bladder cancer, prostatic cancer, testicular tumor, osteosarcoma and soft tissue sarcoma, leukemia, malignant lymphoma, multiple myeloma, skin cancer, and brain tumor.

The present invention will next be described in detail with reference to Referential Examples, Comparative Examples, Examples (working examples), Pharmacological Test Examples, and Preparation Examples. However, any of these should not be construed as limiting the invention thereto.

EXAMPLE 1

5'-O-(tert-Butyldimethylsilyl)-2'-cyano-2'-deoxy-1-β-D-arabinofuranosylcytosine (1)

2'-Cyano-2'-deoxy-1-β-D-arabinofuranosylcytosine (hereinafter referred to as CNDAC) (1.02 g, 4.04 mmol) was suspended in pyridine (40 mL). tert-Butyldimethylsilyl chloride (790 mg, 5.25 mmol) was added to the resultant suspension. The mixture was stirred at room temperature for 24 hours under nitrogen. The solvent was removed and the residue was co-boiled twice with toluene and purified through silica gel column chromatography (5% methanol/chloroform), whereby the Compound 1 was obtained as a white solid (1.19 g, 80%).

$^1$H-NMR (DMSO-$d_6$) δ 7.67 (1H, d, J=7.6 Hz), 7.18 (2H, br d), 6.18 (1H, d, J=5.9 Hz), 6.12 (1H, d, J=7.6 Hz), 5.65 (1H, d, J=7.6 Hz), 4.29 (1H, dd, J=13.9 Hz, J=8.1 Hz), 3.84-3.69 (4H, m), 0.81 (9H, s), 0.00, −0.01 (each 3H, each s); FAB-LRMS m/z 367 (MH$^+$).

Anal. Calcd for $C_{16}H_{26}N_4O_4Si$: C, 52.44; H, 7.15; N, 15.29. Found: C, 52.01; H, 7.10; N, 15.02; mp 185° C. (decomp.).

EXAMPLE 2

5'-O-Triisopropylsilyl-2'-cyano-2'-deoxy-1-β-D-arabinofuranosylcytosine (2)

The general procedure of Example 1 was repeated through use of CNDAC (1.01 g, 4.00 mmol) and triisopropylsilyl chloride (1.68 mL, 8.00 mmol), whereby the Compound 2 was obtained as a white solid (720 mg, 44%).

$^1$H-NMR (DMSO-$d_6$) δ 7.76 (1H, d, J=7.3 Hz), 7.26 (2H, br s), 6.28 (1H, d, J=5.9 Hz), 6.22 (1H, d, J=7.6 Hz), 5.72 (1H, d, J=7.6 Hz), 4.44 (1H, ddd, J=13.9 Hz, J=8.1 Hz, J=5.9 Hz), 4.01-3.77 (4H, m), 1.16-1.04 (21H, m); FAB-LRMS m/z 409 (MH$^+$). Anal. Calcd for $C_{19}H_{32}N_4O_4Si$: C, 55.86; H, 7.89; N, 13.71. Found: C, 55.83; H, 7.48; N, 14.10; mp 177° C. (decomp.).

EXAMPLE 3

5'-O-Diethylisopropylsilyl-2'-cyano-2'-deoxy-1-β-D-arabinofuranosylcytosine (3)

The general procedure of Example 1 was repeated through use of CNDAC (1.01 g, 4.00 mmol) and diethylisopropylsilyl chloride (800 μL, 4.36 mmol), whereby the Compound 3 was obtained as a white solid (762 mg, 50%).

$^1$H-NMR (DMSO-$d_6$) δ 7.79 (1H, d, J=7.3 Hz), 7.26 (2H, br s), 6.27 (1H, d, J=5.6 Hz), 6.21 (1H, d, J=7.3 Hz), 5.74 (1H, d, J=7.6 Hz), 4.40 (1H, dd, J=13.9 Hz, J=7.9 Hz), 3.96-3.76 (4H, m), 0.97-0.92 (13H, m), 0.67-0.58 (4H, m); FAB-LRMS m/z 381 (MH$^+$). Anal. Calcd for $C_{17}H_{28}N_4O_4Si$: C, 53.66; H, 7.42; N, 14.72. Found: C, 55.69; H, 7.16; N, 14.89; mp 175° C. (decomp.).

EXAMPLE 4

5'-O-Cyclohexyldimethylsilyl-2'-cyano-2'-deoxy-1-β-D-arabinofuranosylcytosine (4)

The general procedure of Example 1 was repeated through use of CNDAC (1.00 g, 3.96 mmol) and cyclohexyldimethylsilyl chloride (808 μL, 4.36 mmol), whereby the Compound 4 was obtained as a white solid (1.03 g, 66%).

$^1$H-NMR (DMSO-$d_6$) δ 7.71 (1H, d, J=7.6 Hz), 7.21 (2H, br d), 6.19 (1H, d, J=5.3 Hz), 6.15 (1H, d, J=7.3 Hz), 5.68 (1H, d, J=7.6 Hz), 4.30 (1H, dd, J=13.9 Hz, J=7.9 Hz), 3.83-3.66 (4H, m), 1.62 (5H, m), 1.14-1.01 (5H, m), 0.65 (1H, m), 0.00 (6H, s); FAB-LRMS m/z 393 (MH$^+$). Anal. Calcd for $C_{18}H_{28}N_4O_4Si$: C, 55.08; H, 7.19; N, 14.27. Found: C, 54.96; H, 7.04; N, 14.49; mp 152-153° C.

EXAMPLE 5

5'-O-(tert-Butyldiphenylsilyl)-2'-cyano-2'-deoxy-1-β-D-arabinofuranosylcytosine (5)

The general procedure of Example 1 was repeated through use of CNDAC (1.00 g, 3.96 mmol) and tert-butyldiphenylsilyl chloride (1.42 mL, 5.54 mmol), whereby the Compound 5 was obtained as a white solid (1.68 g, 3.42 mmol, 86%).

$^1$H-NMR (DMSO-$d_6$) δ 7.70 (1H, d, J=7.6 Hz), 7.64 (4H, m), 7.50-7.40 (6H, m), 7.27 (2H, d, J=7.6 Hz), 6.34 (1H, d, J=5.6 Hz), 6.25 (1H, d, J=7.6 Hz), 5.59 (1H, d, J=7.6 Hz), 4.55 (1H, dd, J=13.7 Hz, J=7.6 Hz), 3.97-3.84 (4H, m), 1.02 (9H, s); FAB-LRMS m/z 491 (MH$^+$). Anal. Calcd for $C_{26}H_{30}N_4O_4Si$: C, 63.65; H, 6.16; N, 11.42. Found: C, 63.38; H, 6.18; N, 11.60; mp 187° C.

EXAMPLE 6

5'-O-Dimethylthexylsilyl-2'-cyano-2'-deoxy-1-β-D-arabinofuranosylcytosine (6)

The general procedure of Example 1 was repeated through use of CNDAC (1.00 g, 3.96 mmol) and dimethylthexylsilyl chloride (1.01 mL, 5.15 mmol), whereby the Compound 6 was obtained as a white solid (905 mg, 58%).

$^1$H-NMR (DMSO-$d_6$) δ 7.60 (1H, d, J=7.3 Hz), 7.15 (2H, br d), 6.14 (1H, d, J=5.9 Hz), 6.08 (1H, d, J=7.3 Hz), 5.63 (1H, d, J=7.6 Hz), 4.24 (1H, dd, J=13.9 Hz, J=7.3 Hz), 3.79-3.64 (4H, m), 1.49 (1H, m), 0.76-0.73 (12H, m), 0.07, 0.00 (each 6H, s); FAB-LRMS m/z 395 (MH$^+$). Anal. Calcd for $C_{18}H_{30}N_4O_4Si$: C, 54.80; H, 7.66; N, 14.20.

Found: C, 54.54; H, 7.71; N, 14.12; mp 188° C. (decomp.).

EXAMPLE 7

5'-O-Triisobutylsilyl-2'-cyano-2'-deoxy-1-β-D-arabinofuranosylcytosine (7)

The general procedure of Example 1 was repeated through use of CNDAC (1.00 g, 3.96 mmol) and triisobutylsilyl chloride (1.28 mL, 4.75 mmol), whereby the Compound 7 was obtained as a white solid (1.68 g, 94%).

$^1$H-NMR (DMSO-$d_6$) 7.73 (1H, d, J=7.6 Hz), 7.28 (2H, br d), 6.22 (1H, d, J=5.9 Hz), 6.19 (1H, d, J=7.3 Hz), 5.74 (1H, d, J=7.6 Hz), 4.37 (1H, dd, J=13.7 Hz, J=7.1 Hz), 3.89-3.76 (4H, m), 1.80 (3H, m), 0.93 (18H, m), 0.63 (6H, m); FAB-LRMS m/z 451 (MH$^+$).

Anal. Calcd for $C_{22}H_{38}N_4O_4Si$: C, 58.64; H, 8.50; N, 12.43. Found: C, 58.49; H, 8.59; N, 12.20; mp 152° C.

EXAMPLE 8

5'-O-Triphenylsilyl-2'-cyano-2'-deoxy-1-β-D-arabinofuranosylcytosine (8)

The general procedure of Example 1 was repeated through use of CNDAC (1.00 g, 3.96 mmol) and triphenylsilyl chloride (1.40 g, 4.75 mmol), whereby the Compound 8 was obtained as a white solid (1.14 g, 56%).

$^1$H-NMR (DMSO-$d_6$) δ 7.62-7.42 (16H, m), 7.23 (2H, br d), 6.30 (1H, d, J=5.6 Hz), 6.22 (1H, d, J=7.6 Hz), 5.39 (1H, d, J=6.9 Hz), 4.53 (1H, dd, J=13.9 Hz, J=7.6 Hz), 4.10-3.95 (2H, m), 3.84 (2H, m); FAB-LRMS m/z 511 (MH$^+$). Anal.

Calcd for C$_{28}$H$_{26}$N$_4$O$_4$Si: C, 65.86; H, 5.13; N, 10.97. Found: C, 65.26; H, 5.20; N, 10.89; mp 203° C. (decomp.).

EXAMPLE 9

5'-O-Tribenzylsilyl-2'-cyano-2'-deoxy-1-β-D-arabinofuranosylcytosine (9)

The general procedure of Example 1 was repeated through use of CNDAC (1.00 g, 3.96 mmol) and tribenzylsilyl chloride (1.60 g, 4.75 mmol), whereby the Compound 9 was obtained as a white solid (1.64 g, 75%).

$^1$H-NMR (DMSO-d$_6$) δ 7.40 (1H, d, J=7.6 Hz), 7.24-6.97 (17H, m), 6.24 (1H, d, J=5.8 Hz), 6.21 (1H, d, J=7.6 Hz), 5.53 (1H, d, J=7.6 Hz), 4.38 (1H, dd, J=13.5 Hz, J=7.6 Hz), 3.93 (1H, dd, J=11.7 Hz, J=2.1 Hz), 3.85-3.73 (3H, m), 2.14 (6H, s), FAB-LRMS (negative) m/z 551 (M-H)$^−$. Anal. Calcd for C$_{31}$H$_{32}$N$_4$O$_4$Si: C, 67.37; H, 5.84; N, 10.14. Found: C, 67.12; H, 5.64; N, 10.54; mp 188° C. (decomp.).

EXAMPLE 10

5'-O-(Dimethyl-n-octylsilyl)-2'-cyano-2'-deoxy-1-β-D-arabinofuranosylcytosine (10)

CNDAC (1.00 g, 3.96 mmol) was dissolved in N,N-dimethylformamide (hereinafter referred to as DMF) (40 mL), and imidazole (593 mg, 8.72 mmol) and dimethyl-n-octylchlorosilane (1.04 mL, 4.36 mmol) were added thereto. The resultant mixture was stirred at room temperature for 3 hours under nitrogen. The reaction mixture was partitioned between ethyl acetate and water, the formed organic layer was washed with saturated brine, and then the thus-washed organic layer was dried over sodium sulfate anhydrate. The solvent was removed and the residue was purified through neutral silica gel column chromatography (5-12% methanol/chloroform), whereby the Compound 10 was obtained as a white solid (940 mg, 56%).

$^1$H-NMR (DMSO-d$_6$) δ 7.87 (1H, d, J=7.6 Hz), 7.34 (2H, br d), 6.31 (2H, m), 5.82 (1H, d, J=7.4 Hz), 4.44 (1H, dd, J=13.4 Hz, J=7.7 Hz), 3.97-3.81 (4H, m), 1.34 (12H, m), 0.93 (3H, m), 0.68 (2H, m), 0.19 (6H, s); FAB-LRMS m/z 423 (MH$^+$). Anal. Calcd for C$_{20}$H$_{34}$N$_4$O$_4$Si.0.2H$_2$O: C, 56.36; H, 8.14; N, 13.15. Found: C, 56.36; H, 7.92; N, 13.67; mp 142° C.

EXAMPLE 11

5'-O-Dimethylphenylsilyl-2'-cyano-2'-deoxy-1-β-D-arabinofuranosylcytosine (11)

The general procedure of Example 10 was repeated through use of CNDAC (1.00 g, 3.96 mmol) and dimethylphenylsilyl chloride (723 μL, 4.36 mmol), whereby the Compound 11 was obtained as a white solid (624 mg, 40%).

$^1$H-NMR (DMSO-d$_6$) δ 7.72 (1H, d, J=7.6 Hz), 7.57 (2H, m), 7.41 (3H, m), 7.25 (2H, br d), 6.24 (1H, d, J=5.6 Hz), 6.20 (1H, d, J=7.3 Hz), 5.64 (1H, d, J=7.6 Hz), 4.38 (1H, m), 3.92-3.77 (4H, m), 0.37 (6H, s); FAB-LRMS m/z 387 (MH$^+$). Anal. Calcd for C$_{18}$H$_{22}$N$_4$O$_4$Si.0.5H$_2$O: C, 54.67; H, 5.86; N, 14.17. Found: C, 54.77; H, 7.80; N, 14.01; mp 139-140° C.

EXAMPLE 12

5'-O-Dimethylthexylsilyl-2'-cyano-2'-deoxy-1-β-D-ribofuranosylcytosine (12)

2'-Cyano-2'-deoxy-1-β-D-ribofuranosylcytosine trifluoroacetate (55 mg, 0.150 mmol) was dissolved in DMF (0.5 mL), and imidazole (41 mg, 0.602 mmol) and dimethylthexylsilyl chloride (29.4 μL, 0.15 mmol) were added thereto. The resultant mixture was stirred at room temperature for 5 hours under nitrogen. The reaction mixture was partitioned between ethyl acetate and water, the formed organic layer was washed with saturated brine, and then the thus-washed organic layer was dried over sodium sulfate anhydrate. The solvent was removed and the residue was purified through silica gel column chromatography (7-10% methanol/chloroform), whereby the Compound 12 was obtained as a white foam (59 mg, 100%).

$^1$H-NMR (DMSO-d$_6$) δ 7.61 (1H, d, J=7.6 Hz), 7.32 (2H, br s), 6.29 (1H, d, J=5.6 Hz), 6.28 (1H, d, J=7.3 Hz), 5.74 (1H, d, J=7.6 Hz), 4.26-4.32 (1H, m), 3.91-3.95 (1H, m), 3.76 (1H, dd, J=3.6 Hz, J=11.5 Hz), 3.71 (1H, dd, J=3.6 Hz, J=11.5 Hz), 3.56-3.60 (1H, m), 1.53-1.63 (1H, m), 0.81-0.86 (12H, m), 0.00 (6H, s); FAB-LRMS m/z 395 (MH$^+$). Anal. Calcd for C$_{18}$H$_{30}$N$_4$O$_4$Si: C, 54.80; H, 7.66; N, 14.20. Found: C, 54.62; H, 7.59; N, 14.47; mp 187-187.5° C.

EXAMPLE 13

5'-O-Dimethylthexylsilyl-3'-O-(tert-butyldimethylsilyl)-2'-cyano-2'-deoxy-1-β-D-arabinofuranosylcytosine (13)

The Compound 6 (79 mg, 0.200 mmol) was dissolved in DMF (2 mL), and imidazole (54 mg, 0.793 mmol) and tert-butyldimethylsilyl chloride (60 mg, 0.40 mmol) were added thereto, the mixture was stirred at room temperature for 24 hours under nitrogen. The reaction mixture was partitioned between ethyl acetate and water, the formed organic layer was washed with saturated brine, and then the thus-washed organic layer was dried over sodium sulfate anhydrate. The solvent was removed and the residue was purified through silica gel column chromatography (2% methanol/chloroform), whereby the Compound 13 was obtained as a white foam (74 mg, 73%).

$^1$H-NMR (DMSO-d$_6$) δ 7.62 (1H, d, J=7.6 Hz), 7.30 (2H, br s), 6.23 (1H, d, J=7.6 Hz), 5.77 (1H, d, J=7.6 Hz), 4.53 (1H, t, J=7.6 Hz), 3.92 (2H, m), 3.77 (2H, m), 1.61 (2H, m), 0.86 (21H, m) 0.12 (12H, m); FAB-LRMS m/z 509 (MH$^+$).

EXAMPLE 14

3',5'-Bis-O-dimethylthexylsilyl-2'-cyano-2'-deoxy-1-β-D-arabinofuranosylcytosine (14)

CNDAC hydrochloride (3.40 g, 11.8 mmol) was dissolved in DMF (100 mL), and imidazole (5.42 g, 94.4 mmol) and dimethylthexylsilyl chloride (9.27 mL, 47.2 mmol) were added thereto. The resultant mixture was stirred at 50° C. for 20 hours under nitrogen. The reaction mixture was concentrated under reduced pressure, and the residue was partitioned between ethyl acetate and water. The formed organic layer was washed with saturated brine, and then the thus-washed organic layer was dried over sodium sulfate anhydrate. The solvent was removed and the residue was purified through silica gel column chromatography (0-10% methanol/chloroform), whereby the Compound 14 was obtained as a white foam (4.80 g, 76%).

$^1$H-NMR (DMSO-$_6$) δ 7.62 (1H, d, J=7.6 Hz), 7.29 (2H, br s), 6.23 (1H, d, J=7.6 Hz), 5.77 (1H, d, J=7.6 Hz), 4.53 (1H, dd, J=7.6 Hz, J=7.3 Hz), 3.91 (2H, m), 3.83-3.71 (2H, m), 1.60 (2H, m), 0.85 (24H, m), 0.14 (12H, m).

EXAMPLE 15

3',5'-Bis-O-diethylisopropylsilyl-2'-cyano-2'-deoxy-1-β-D-arabinofuranosylcytosine (15)

The general procedure of Example 13 was repeated through use of CNDAC (1.00 g, 3.96 mmol) and diethylisopropylsilyl chloride (1.83 mL, 10.0 mmol), whereby the Compound 15 was obtained as a white foam (1.96 g, 97%).

$^1$H-NMR (DMSO-$d_6$) δ 7.76 (1H, d, J=7.4 Hz), 7.34 (2H, br s), 6.30 (1H, d, J=7.6 Hz), 5.82 (1H, d, J=7.4 Hz), 4.68 (1H, dd, J=7.7 Hz, J=7.4 Hz), 4.03 (2H, m), 3.87 (2H, m), 1.01 (26H, m), 0.71 (8H, m); FAB-LRMS m/z 509 (MH$^+$).

EXAMPLE 16

3',5'-Bis-O-triisobutylsilyl-2'-cyano-2'-deoxy-1-β-D-arabinofuranosylcytosine (16)

The general procedure of Example 14 was repeated through use of CNDAC (1.00 g, 3.96 mmol) and triisobutylsilyl chloride (3.22 mL, 12.0 mmol), whereby the Compound 16 was obtained as a white foam (2.48 g, 96%).

$^1$H-NMR (DMSO-$d_6$) δ 7.65 (1H, d, J=7.4 Hz), 7.30 (2H, br d), 6.19 (1H, d, J=7.3 Hz), 5.76 (1H, d, J=7.4 Hz), 4.58 (1H, dd, J=6.9 Hz, J=6.8 Hz), 3.87 (3H, m), 3.75 (1H, dd, J=3.1 Hz, J=11.5 Hz), 1.88-1.72 (6H, m), 0.94 (36H, m), 0.75-0.59 (12H, m); FAB-LRMS m/z 649 (MH$^+$).

EXAMPLE 17

3',5'-Bis-O-(dimethyl-n-octylsilyl)-2'-cyano-2'-deoxy-1-β-D-arabinofuranosylcytosine (17)

The general procedure of Example 14 was repeated through use of CNDAC (1.00 g, 3.96 mmol) and dimethyl-n-octylsilyl chloride (2.38 mL, 10.0 mmol), whereby the Compound 17 was obtained as a colorless oil (970 mg, 41%).

$^1$H-NMR (DMSO-$d_6$) δ 7.71 (1H, d, J=7.4 Hz), 7.26 (2H, br d), 6.19 (1H, d, J=7.4 Hz), 5.74 (1H, d, J=7.6 Hz), 4.52 (1H, dd, J=7.6 Hz, J=7.7 Hz), 3.92 (1H, dd, J=7.9 Hz, J=7.6 Hz), 3.86-3.67 (3H, m), 1.25 (24H, m), 0.82 (6H, m), 0.60 (4H, m), 0.10 (12H, m).

EXAMPLE 18

3',5'-O-(Di-tert-butylsilanediyl)-2'-cyano-2'-deoxy-1-β-D-arabinofuranosylcytosine (18)

CNDAC (504 mg, 2.01 mmol) and silver nitrate (747 mg, 4.42 mmol) was dissolved in DMF (20 mL), and di-tert-butylsilyl bis(trifluoromethanesulfonate) (712 μL, 2.21 mmol) was added thereto under cooling with ice. The reaction mixture was stirred at room temperature for 30 minutes under nitrogen, triethylamine (612 μL, 4.42 mmol) was added thereto, and the reaction mixture was stirred again for 5 minutes. The reaction mixture was concentrated under reduced pressure, and the residue was partitioned between ethyl acetate and water. The formed organic layer was washed with water and saturated brine, and the thus-washed organic layer was dried over sodium sulfate anhydrate. The solvent was removed, and chloroform was added to the residue, followed by filtration through Celite for removal of insoluble matter. The filtrate was concentrated, and the residue was purified through silica gel column chromatography (2-5% methanol/chloroform), followed by crystallization from hexane, whereby the Compound 18 was obtained as a white solid (712 mg, 91%).

$^1$H-NMR (DMSO-$d_6$) δ 7.72 (1H, d, J=6.9 Hz), 7.33 (2H, br d), 6.44 (1H, br s), 5.79 (1H, d, J=7.3 Hz), 4.33 (2H, m), 4.06 (2H, m), 3.81 (1H, m), 1.04, 0.97 (each 9H, each s); FAB-LRMS m/z 393 (MH$^+$).

Anal. Calcd for $C18H_{28}N_4O_4Si \cdot 1.3H_2O$: C, 51.98; H, 7.42; N, 13.47.

Found: C, 52.00; H, 6.98; N, 12.94; mp 139-140° C.

EXAMPLE 19

3'-O-Dimethylthexylsilyl-2'-cyano-2'-deoxy-1-β-D-arabinofuranosylcytosine (19)

Compound 14 (5.11 g, 9.52 mmol) was dissolved in tetrahydrofuran (hereinafter referred to as THF) (50 mL). An 80% Aqueous trifluoroacetic acid (50 mL) was added thereto. The mixture was stirred at room temperature for 3 hours. The reaction mixture was concentrated under reduced pressure. The residue was co-boiled three times with ethanol, and subsequently chloroform was added thereto. The white solid that precipitated was obtained by filtration. The solid was dissolved in a 10% methanol-chloroform solvent mixture, and the resultant mixture was washed with saturated aqueous sodium hydrogencarbonate. The formed organic layer was washed with water and saturated brine, and the thus-washed organic layer was dried over sodium sulfate anhydrate. The solvent was removed, and the residue was crystallized from hexane, to thereby yield the Compound 19 as a white solid (3.04 g, 81%).

$^1$H-NMR (DMSO-$d_6$) δ 7.79 (1H, d, J=7.6 Hz), 7.26 (2H, br d), 6.19 (1H, d, J=7.6 Hz), 5.77 (1H, d, J=7.6 Hz), 5.19 (1H, dd, J=5.3 Hz, J=4.9 Hz), 4.57 (1H, dd, J=6.9 Hz, J=7.3 Hz), 3.85 (1H, dd, J=7.6 Hz, J=7.3 Hz), 3.74 (2H, m), 3.56 (1H, m), 1.59 (1H, m), 0.84 (12H, m), 0.18, 0.15 (each 3H, each s); FAB-LRMS m/z 395 (MH$^+$). Anal. Calcd for $C_{18}H_{30}N_4O_4Si$: C, 54.80; H, 7.66; N, 14.20.

Found: C, 54.54; H, 7.70; N, 13.82; mp 159-161° C.

EXAMPLE 20

3'-O-Dimethylthexylsilyl-2'-cyano-2'-deoxy-1-β-D-arabinofuranosylcytosine methanesulfonate (20)

Compound 14 (3.00 g, 5.11 mmol), synthesized in a manner similar to Example 14 except that purification was not performed, was dissolved in ethanol (10 mL). Methanesulfonic acid (800 μl) was added thereto. The mixture was stirred at room temperature for 2.5 hours. Ethyl acetate (10 mL) was added to the reaction mixture, and the white solid that precipitated was obtained by filtration, to thereby yield the Compound 20 as a white solid (1.42 g, 57%).

$^1$H-NMR (DMSO-$d_6$) δ 9.58 (1H, br s), 8.64 (1H, br s), 8.23 (1H, d, J=7.9 Hz), 6.23 (1H, d, J=7.3 Hz), 6.17 (1H, d, J=7.9 Hz), 4.60 (1H, dd, J=7.6 Hz, J=7.9 Hz), 4.08 (1H, dd, J=7.6 Hz, J=7.9 Hz), 3.80 (2H, m), 3.58 (1H, dd, J=3.6 Hz, J=12.5 Hz), 2.37 (3H, s), 1.59 (1H, m), 0.85 (12H, m), 0.18, 0.16 (each 3H, each s); FAB-LRMS (negative) m/z 489

(M-H)⁻; Anal. Calcd for $C_{19}H_{34}N_4O_7SSi$: C, 46.51; H, 6.98; N, 11.42. Found: C, 46.46; H, 7.02; N, 11.42; mp 203-204° C.

EXAMPLE 21

3'-O-Diethylisopropylsilyl-2'-cyano-2'-deoxy-1-β-D-arabinofuranosylcytosine (21)

An 80% aqueous acetic acid solution (20 mL) was added to Compound 15 (400 mg, 0.786 mmol), and the mixture was stirred at room temperature for 5 hours. The reaction mixture was diluted with ethyl acetate, and washed with saturated aqueous sodium hydrogencarbonate. The formed organic layer was sequentially washed with water and saturated brine, and the thus-washed organic layer was dried over sodium sulfate anhydrate. After removal of solvent, and the residue was purified through neutral silica gel column chromatography (2 to 15% methanol/chloroform), followed by crystallization from hexane, whereby the Compound 21 was obtained as a white solid (116 mg, 39%).

$^1$H-NMR (DMSO-$d_6$) δ 7.79 (1H, d, J=7.6 Hz), 7.25 (2H, br d), 6.17 (1H, d, J=7.3 Hz), 5.77 (1H, d, J=7.4 Hz), 5.20 (1H, t, J=5.3 Hz), 4.60 (1H, dd, J=6.9 Hz, J=6.8 Hz), 3.86 (1H, dd, J=6.9 Hz, J=7.3 Hz), 3.75 (2H, m), 3.57 (1H, m), 0.97 (13H, m), 0.66 (4H, m); FAB-LRMS m/z 381 (MH⁺). Anal. Calcd for $C_{17}H_{28}N_4O_4Si.0.7H_2O$: C, 51.94; H, 7.54; N, 14.25. Found: C, 52.06; H, 7.33; N, 13.87; mp 161-163° C.

EXAMPLE 22

3'-O-Triisobutylsilyl-2'-cyano-2'-deoxy-1-β-D-arabinofuranosylcytosine (22)

Compound 16 (1.30 g, 2.00 mmol) was dissolved in THF (16 mL). An 80% aqueous trifluoroacetic acid solution (4 mL) was added thereto, and the resultant mixture was stirred at room temperature for 30 minutes. The reaction mixture was diluted with ethyl acetate, and washed with saturated aqueous sodium hydrogencarbonate. The formed organic layer was sequentially washed with water and saturated brine, and the thus-washed organic layer was dried over sodium sulfate anhydrate. After removal of solvent, the residue was purified through silica gel column chromatography (5 to 10% methanol/chloroform), followed by crystallization from hexane, whereby the Compound 22 was obtained as a white solid (270 mg, 30%).

$^1$H-NMR (DMSO-$d_6$) δ 7.80 (1H, d, J=7.6 Hz), 7.27 (2H, br d), 6.16 (1H, d, J=7.3 Hz), 5.78 (1H, d, J=7.4 Hz), 5.21 (1H, dd, J=5.3 Hz, J=4.9 Hz), 4.63 (1H, dd, J=6.6 Hz, J=6.4 Hz), 3.85-3.71 (3H, m), 3.58 (1H, m), 1.81 (3H, m), 0.95 (18H, m), 0.69 (6H, m); FAB-LRMS m/z 451 (MH⁺). Anal. Calcd for $C_{22}H_{38}N_4O_4Si-.0.7H_2O$: C, 57.04; H, 8.57; N, 12.09. Found: C, 56.98; H, 8.35; N, 11.96; mp 101-102° C.

EXAMPLE 23

3'-O-(Dimethyl-n-octylsilyl)-2'-cyano-2'-deoxy-1-β-D-arabinofuranosylcytosine (23)

Compound 17 (573 mg, 0.966 mmol) was dissolved in THF (5 mL). A 50% aqueous acetic acid solution (5 mL) was added thereto, and the resultant mixture was stirred for 20 minutes under cooling with ice. The reaction mixture was diluted with ethyl acetate, and washed with saturated aqueous sodium hydrogencarbonate. The formed organic layer was sequentially washed with water and saturated brine, and the thus-washed organic layer was dried over sodium sulfate anhydrate. After removal of solvent, the residue was purified through neutral silica gel column chromatography (2 to 10% methanol/chloroform), whereby the Compound 23 was obtained as a white solid (111 mg, 27%).

$^1$H-NMR (DMSO-$d_6$) δ 7.79 (1H, d, J=7.3 Hz), 7.26 (2H, br d), 6.18 (1H, d, J=7.3 Hz), 5.77 (1H, d, J=7.6 Hz), 5.17 (1H, dd, J=5.3 Hz, J=4.9 Hz), 4.55 (1H, t, J=7.3 Hz), 3.86 (1H, dd, J=7.6 Hz, J=7.3 Hz), 3.72 (2H, m), 3.56 (1H, m), 1.25 (12H, m), 0.84 (3H, m), 0.60 (2H, m), 0.14 (6H, s); FAB-LRMS m/z 423 (MH⁺).

Anal. Calcd for $C_{20}H_{34}N_4O_4Si$: C, 56.84; H, 8.11; N, 13.26. Found: C, 56.83; H, 8.16; N, 13.12; mp 153-154° C.

EXAMPLE 24

4-N-(tert-Butoxycarbonyl)-2-cyano-2'-deoxy-1-β-D-arabinofuranosylcytosine (24a)

CNDAC (10.0 g, 39.6 mmol) was dissolved in DMF (250 mL). Di-tert-butyl dicarbonate (26.0 g, 119 mmol) was added thereto, and the resultant mixture was stirred under nitrogen for 28 hours at 50° C. The reaction mixture was left to cool, and concentrated under reduced pressure. The residue was purified through silica gel column chromatography (5 to 10% methanol/chloroform), whereby the Compound 24a was obtained as a white solid (8.30 g, 59%).

$^1$H-NMR (DMSO-$d_6$) δ 10.47 (1H, s), 8.31 (1H, d, J=7.6 Hz), 7.07 (1H, d, J=7.8 Hz), 6.26 (1H, d, J=5.6 Hz), 6.20 (1H, d, J=7.1 Hz), 5.24 (1H, m), 4.43 (1H, m), 3.90 (1H, m), 3.83 (1H, m), 3.76 (1H, m), 3.64 (1H, m), 1.47 (9H, s); FAB-LRMS m/z 353 (MH⁺). Anal. Calcd for $C_{15}H_{20}N_4O_6.1.3H_2O$: C, 47.95; H, 6.06; N, 14.91. Found: C, 48.04; H, 5.95; N, 14.46; mp 120-122° C. (decomp.).

4-N-(tert-Butoxycarbonyl)-5'-O-dimethoxytrityl-2'-cyano-2'-deoxy-1-β-D-arabinofuranosylcytosine (24b)

Compound 24a (4.00 g, 11.4 mmol) was dissolved in pyridine (70 mL). Dimethoxytrityl chloride (4.65 g, 13.7 mmol) was added thereto, and the resultant mixture was stirred under nitrogen at room temperature for 22 hours. The reaction mixture was quenched with methanol, and the solvent was removed under reduced pressure. The residue was co-boiled with toluene twice, and the co-boiled product was dissolved in chloroform, followed by sequentially washing water and saturated brine. The thus-washed organic layer was dried over sodium sulfate anhydrate, and the solvent was removed. The residue was purified through silica gel column chromatography (0 to 2.5% methanol/chloroform), whereby the Compound 24b was obtained as an yellow foam (6.64 g, 89%).

$^1$H-NMR (DMSO-$d_6$) δ 10.48 (1H, s), 8.27 (1H, d, J=7.8 Hz), 7.35 (4H, m), 7.26 (5H, m), 6.90 (5H, m), 6.40 (1H, d, J=5.9 Hz), 6.27 (1H, d, J=7.3 Hz), 4.60 (1H, dd, J=14.4 Hz, J=8.1 Hz), 3.96 (1H, m), 3.75 (6H, s), 3.46-3.36 (2H, m), 1.46 (9H, s); FAB-LRMS (negative) m/z 653 (M-H)⁻.

4-N-(tert-Butoxycarbonyl)-3'-O-(tert-butyldimethylsilyl)-2'-cyano-2'-deoxy-1-β-D-arabinofuranosylcytosine (24c)

Compound 24b (6.58 g, 10.1 mmol) was dissolved in DMF (60 mL). Imidazole (2.73 g, 40.3 mmol) and tert-butyldimethylsilyl chloride (3.03 g, 20.1 mmol) were added thereto, and the resultant mixture was stirred under nitrogen at room temperature for 16 hours. The reaction mixture was concentrated under reduced pressure, and the residue was partitioned between ethyl acetate and water. The organic layer was washed with saturated brine, followed by drying over sodium sulfate anhydrate. After removal of solvent, an 80% aqueous acetic acid solution was added to the residue, and the resultant mixture was stirred for 2 hours at room temperature. The reaction mixture was concentrated under reduced pressure, and the residue was co-boiled with ethanol three times. The resultant mixture was partitioned between ethyl acetate and water. The formed organic layer was sequentially washed with water and saturated brine. The thus-washed organic layer was dried over sodium sulfate anhydrate, and the solvent was removed. The residue was purified through silica gel column chromatography (0 to 2% methanol/chloroform), whereby the Compound 24c was obtained as a pale yellow foam (4.11 g, 88%).

$^1$H-NMR (CDCl$_3$) δ 8.03 (1H, d, J=7.9 Hz), 7.42 (1H, br s), 7.31 (1H, d, J=7.6 Hz), 6.25 (1H, d, J=6.6 Hz), 4.71 (1H, m), 4.01 (2H, m), 3.85 (1H, m), 3.68 (1H, m), 2.26 (1H, br s), 1.51 (9H, s), 0.91 (9H, s), 0.18, 0.15 (each 3H, each s); FAB-LRMS m/z 467 (MH$^+$).

3'-O-(tert-Butyldimethylsilyl)-2'-cyano-2'-deoxy-1-β-D-arabinofuranosylcytosine trifluoroacetate (24)

Compound 24c (620 mg, 1.33 mmol) was dissolved in dichloromethane (10 mL). Trifluoroacetic acid (10 mL) was added thereto under cooling with ice, and the resultant mixture was stirred at room temperature for 90 minutes. The reaction mixture was diluted with ethanol, and concentrated under reduced pressure. The residue was co-boiled with ethanol three times, followed by addition of chloroform. The white solid that precipitated was separated through filtration, whereby the Compound 24 was obtained as a white solid (560 mg, 88%).

$^1$H-NMR (DMSO-d$_6$) δ 8.91 (1H, br s), 8.25 (1H, br s), 8.10 (1H, d, J=7.9 Hz), 6.21 (1H, d, J=7.3 Hz), 6.04 (1H, d, J=7.9 Hz), 4.59 (1H, dd, J=7.7 Hz, J=7.6 Hz), 4.03 (1H, dd, J=7.9 Hz, J=7.4 Hz), 3.83-3.55 (4H, m), 0.87 (9H, s), 0.14, 0.13 (each 3H, each s); FAB-LRMS (negative) m/z 479 (M-H)$^-$. Anal. Calcd for C$_{18}$H$_{27}$F$_3$N$_4$O$_6$Si: C, 44.99; H, 5.66; N, 11.66. Found: C, 44.89; H, 5.58; N, 11.61; mp 163-165° C.

EXAMPLE 25

4-N-(tert-Butoxycarbonyl)-5'-O-dimethoxytrityl-3'-O-dimethylthexylsilyl-2'-cyano-2'-deoxy-1-β-D-arabinofuranosylcytosine (25a)

Compound 24b (1.20 g, 1.83 mmol) was dissolved in DMF (15 mL). Imidazole (1.50 g, 29.4 mmol) and dimethylthexylsilyl chloride (2.87 mL, 14.7 mmol) were added thereto, and the resultant mixture was stirred under nitrogen for 40 hours at 50° C. The reaction mixture was concentrated under reduced pressure, and the residue was partitioned between ethyl acetate and water. The formed organic layer was washed with saturated brine, followed by drying over sodium sulfate anhydrate. The solvent was removed, and the residue was purified through silica gel column chromatography (hexane:ethyl acetate=3:1 to 1:1), whereby the Compound 25a was obtained as a white foam (1.25 g, 86%).

$^1$H-NMR (CDCl$_3$) δ 8.15 (1H, d, J=7.6 Hz), 7.43-7.22 (9H, m), 7.13 (1H, d, J=7.6 Hz), 6.86 (4H, m), 6.33 (1H, d, J=6.3 Hz), 4.67 (1H, t, J=5.6 Hz), 3.99 (1H, m), 3.81 (6H, s), 3.63 (2H, m), 3.35 (1H, m), 1.51 (9H, s), 0.77 (12H, m), 0.15, −0.07 (each 3H, each s); FAB-LRMS (negative) m/z 795 (M-H)$^-$.

3'-O-Dimethylthexylsilyl-2'-cyano-2'-deoxy-1-β-D-arabinofuranosylcytosine trifluoroacetate (25)

Compound 25a (1.23 g, 1.54 mmol) was dissolved in dichloromethane (10 mL). Trifluoroacetic acid (10 mL) was added thereto under cooling with ice, and the resultant mixture was stirred at room temperature for 3 hours. The reaction mixture was diluted with ethanol, and concentrated under reduced pressure. The residue was co-boiled with ethanol three times, followed by addition of chloroform.

The white solid that precipitated was separated through filtration, whereby the Compound 25 was obtained as a white solid (613 mg, 78%).

$^1$H-NMR (DMSO-d$_6$) δ 8.11 (1H, m), 6.22 (1H, d, J=7.6 Hz), 6.05 (1H, m), 4.59 (1H, t, J=7.6 Hz), 4.01 (1H, t, J=7.6 Hz), 3.78 (2H, m), 1.59 (1H, m), 0.85 (12H, m), 0.18, 0.16 (each 3H, each s); FAB-LRMS (negative) m/z 507 (M-H)$^-$. Anal. Calcd for C$_{20}$H$_{31}$F$_3$N$_4$O$_6$Si.0.2H$_2$O: C, 46.90; H, 6.18; N, 10.94. Found: C, 46.76; H, 6.10; N, 10.67; mp 151-154° C.

EXAMPLE 26

3'-O-Dimethylthexylsilyl-2'-cyano-2'-deoxy-1-β-D-arabinofuranosylcytosine hydrochloride (26)

Compound 25 (720 mg, 1.42 mmol) was dissolved in a 10% methanol/chloroform solvent mixture (100 mL), followed by washing with saturated aqueous sodium hydrogencarbonate (70 mL). The formed organic layer was sequentially washed with water and saturated brine, and the thus-washed organic layer was dried over sodium sulfate anhydrate. After removal of solvent, the residue was dissolved in chloroform (30 mL), and 4N hydrochloric acid/dioxane (354 µL, 1.42 mmol) was added dropwise thereto. The formed white precipitate was separated through filtration, followed by washing with chloroform and drying, whereby the Compound 26 was obtained as a white solid (552 mg, 91%).

$^1$H-NMR (DMSO-d$_6$) δ 9.60 (1H, br s), 8.59 (1H, br s), 8.19 (1H, d, J=7.6 Hz), 6.19 (1H, d, J=7.6 Hz), 6.16 (1H, d, J=7.9 Hz), 4.57 (1H, t, J=7.6 Hz), 4.04 (1H, dd, J=7.6 Hz, J=7.9 Hz), 3.77 (2H, m), 3.55 (1H, m), 1.55 (1H, m), 0.81 (12H, m), 0.15, 0.13 (each 3H, each s); FAB-LRMS (negative) m/z 429 (M-H)$^-$. Anal. Calcd for C$_{18}$H$_{31}$ClN$_4$O$_4$Si: C, 50.16; H, 7.25; N, 13.00. Found: C, 49.82; H, 7.31; N, 12.98; mp 206° C. (decomp.).

EXAMPLE 27

4-N-(tert-Butoxycarbonyl)-5'-O-dimethoxytrityl-3'-O-triisopropylsilyl-2'-cyano-2'-deoxy-1-β-D-arabinofuranosylcytosine (27a)

The procedure of synthesizing Compound 25a was repeated, except that Compound 24b (1.20 g, 1.83 mmol) and triisopropylsilyl chloride (3.11 mL, 14.7 mmol) were employed, whereby the Compound 27a was obtained as a white foam (1.07 g, 72%).

$^1$H-NMR (CDCl$_3$) δ 8.27 (1H, d, J=7.6 Hz), 7.44-6.83 (15H, m), 6.32 (1H, d, J=6.3 Hz), 4.78 (1H, dd, J=4.6 Hz, J=4.3 Hz), 3.80 (6H, s), 3.67 (2H, m), 3.37 (1H, m), 1.51 (9H, s), 0.97 (21H, m); FAB-LRMS (negative) m/z 809 (M-H)$^-$.

3'-O-Triisopropylsilyl-2'-cyano-2'-deoxy-1-β-D-arabinofuranosylcytosine (27)

Compound 27a (1.05 g, 1.29 mmol) was dissolved in dichloromethane (10 mL). Trifluoroacetic acid (10 mL) was added thereto under cooling with ice. The temperature of the reaction mixture was raised to room temperature, followed by stirring for 90 minutes. The reaction mixture was diluted with ethanol, and concentrated under reduced pressure.

The residue was co-boiled with ethanol three times, and the resultant residue was purified through silica gel column chromatography (10% methanol/chloroform), whereby a white solid was obtained. The resultant solid was dissolved in 10% methanol/chloroform solvent mixture, followed by washing with saturated aqueous sodium hydrogencarbonate. The formed organic layer was sequentially washed with water and saturated brine, and the thus-washed layer was dried over sodium sulfate anhydrate, followed by removal of solvent, whereby the Compound 27 was obtained as a white foam (390 mg, 75%).

$^1$H-NMR (DMSO-$d_6$) δ 7.80 (1H, d, J=7.6 Hz), 7.26 (2H, br d), 6.15 (1H, d, J=6.9 Hz), 5.77 (1H, d, J=7.6 Hz), 5.23 (1H, m), 4.73 (1H, t, J=5.9 Hz), 3.84 (1H, m), 3.84 (2H, m), 3.75 (1H, m), 3.60 (1H, m), 1.60 (21H, m); FAB-LRMS m/z 409 (MH$^+$). Anal. Calcd for $C_{19}H_{32}N_4O_4Si \cdot 0.8H_2O$: C, 53.95; H, 8.01; N, 13.25. Found: C, 53.85; H, 7.81; N, 13.01; mp 162-163° C.

EXAMPLE 28

3',5'-Bis-O-dimethylthexylsilyl-2'-cyano-2'-deoxy-1-β-D-ribofuranosylcytosine (28)

2'-Cyano-2'-deoxy-1-β-D-ribofuranosylcytosine trifluoroacetate (183 mg, 0.500 mmol) was dissolved in DMF (2 mL). Imidazole (204 mg, 3.00 mmol) and dimethylthexylsilyl chloride (295 μL, 1.50 mmol) were added thereto, and the resultant mixture was stirred under nitrogen at 60° C. for 13 hours. The reaction mixture was partitioned between ethyl acetate and water, and the formed organic layer was washed with saturated brine, followed by drying over sodium sulfate anhydrate. The solvent was removed, and the residue was purified through silica gel column chromatography (0 to 5% methanol/chloroform), whereby the Compound 28 was obtained as a white foam (248 mg, 92%).

$^1$H-NMR (DMSO-$d_6$) δ 7.58 (1H, d, J=7.3 Hz), 7.32 (2H, br s), 6.25 (1H, d, J=6.9 Hz), 5.75 (1H, d, J=7.6 Hz), 4.46 (1H, dd, J=3.6 Hz, J=5.6 Hz), 3.91 (1H, dd, J=3.6 Hz, J=5.6 Hz), 3.79 (2H, m), 3.67 (1H, m), 1.60 (1H, m), 0.85 (24H, m), 0.18, 0.15 (each 3H, each s), 0.11 (6H, s); FAB-LRMS m/z 537 (MH$^+$)

EXAMPLE 29

3'-O-Dimethylthexylsilyl-2'-cyano-2'-deoxy-1-β-D-ribofuranosylcytosine (29)

Compound 28 (200 mg, 0.372 mmol) was dissolved in ethanol (1 mL). Water (100 μL) and methanesulfonic acid (58 μL, 0.89 mmol) were added thereto, and the resultant mixture was stirred at 40° C. for 3 hours. The reaction mixture was partitioned between ethyl acetate and saturated aqueous sodium hydrogencarbonate. The formed organic layer was sequentially washed with water and saturated brine, followed by drying over sodium sulfate anhydrate. After removal of solvent, the residue was crystallized from methanol-diisopropyl ether, whereby the Compound 29 was obtained as a white solid (95 mg, 65%).

$^1$H-NMR (DMSO-$d_6$) δ 7.70 (1H, d, J=7.4 Hz), 7.32 (2H, br d), 6.29 (1H, d, J=7.9 Hz), 5.77 (1H, d, J=7.6 Hz), 5.19 (1H, t, J=5.3 Hz), 4.54 (1H, dd, J=2.5 Hz, J=5.6 Hz), 3.89 (1H, m), 3.74 (1H, dd, J=5.4 Hz, J=7.9 Hz), 3.54 (2H, m), 1.61 (1H, m), 0.87 (12H, m), 0.18, 0.15 (each 3H, each s); FAB-LRMS m/z 395 (MH$^+$); mp 179-182° C.

EXAMPLE 30

3'-O-Dimethylthexylsilyl-2'-cyano-2'-deoxy-1-β-D-ribofuranosylcytosine methanesulfonate (30)

Compound 29 (52 mg, 0.131 mmol) was dissolved in methanol (150 μL). Methanesulfonic acid (8.5 μL, 0.13 mmol) was added thereto, and the resultant mixture was stirred at 50° C. for 5 minutes. Subsequently, butyl acetate (1.5 mL) was added to the reaction mixture, followed by cooling with ice. The white solid that precipitated was separated through filtration, whereby the Compound 30 was obtained as a white solid (56 mg, 88%).

$^1$H-NMR (DMSO-$d_6$) 9.53 (1H, br s), 8.56 (1H, br s), 8.10 (1H, d, J=7.8 Hz), 6.17 (1H, d, J=6.1 Hz), 6.13 (1H, d, J=7.8 Hz), 4.57 (1H, dd, J=3.9 Hz, J=5.7 Hz), 3.99 (1H, dd, J=3.1 Hz, J=6.6 Hz), 3.88 (1H, t, J=5.9 Hz), 3.68 (1H, dd, J=3.1 Hz, J=12.4 Hz), 3.56 (1H, dd, J=3.0 Hz, J=12.4 Hz), 2.34 (3H, s), 1.60 (1H, m), 0.85 (12H, m), 0.18, 0.15 (each 3H, each s); FAB-LRMS (negative) m/z 489 (M-H)$^-$; mp 211-212° C.

EXAMPLE 31

4-N-(tert-Butoxycarbonyl)-3'-O-dimethylthexylsilyl-2'-cyano-2'-deoxy-1-β-D-arabinofuranosylcytosine (31a)

The procedure of synthesizing Compound 24c was repeated, except that Compound 24b (3.00 g, 4.58 mmol) and dimethylthexylsilyl chloride (5.38 mL, 27.4 mmol) were employed, whereby the Compound 31a was obtained as a white foam (1.78 g, 79%).

$^1$H-NMR (CDCl$_3$) δ 8.04 (1H, d, J=7.6 Hz), 7.45 (1H, br s), 7.31 (1H, d, J=7.6 Hz), 6.28 (1H, d, J=6.3 Hz), 4.73 (1H, t, J=5.0 Hz), 4.04 (2H, m), 3.91 (1H, m), 3.71 (1H, dd, J=4.6 Hz, J=6.3 Hz), 2.16 (1H, m), 1.54 (9H, s), 0.90 (12H, s), 0.26, 0.22 (each 3H, each s).

4-N-(tert-Butoxycarbonyl)-3'-O-dimethylthexylsilyl-5'-O-[N-(tert-butoxycarbonyl)-L-valyl]-2'-cyano-2'-deoxy-1-β-D-arabinofuranosylcytosine (31b)

Compound 31a (742 mg, 1.50 mmol) was dissolved in dichloromethane (20 mL), and Boc-l-Val-OH (652 mg, 3.00 mmol), EDC (575 mg, 3.00 mmol), and DMAP (9 mg, 0.08 mmol) were added thereto, and the resultant mixture was stirred under nitrogen at 0° C. for 4 hours. The reaction mixture was partitioned between ethyl acetate and water, and the formed organic layer was sequentially washed with water and saturated brine, followed by drying over sodium sulfate anhydrate. After removal of solvent, the residue was purified through silica gel column chromatography (0 to 2% methanol/chloroform), whereby the Compound 31b was obtained as a white foam (1.04 g, quant.).

$^1$H-NMR (CDCl$_3$) δ 7.97 (1H, d, J=7.6 Hz), 7.37 (2H, m), 6.22 (1H, d, J=5.9 Hz), 5.01 (1H, d, J=8.2 Hz), 4.56 (2H, m), 4.29 (2H, m), 4.17 (1H, m), 3.72 (1H, dd, J=5.9 Hz, J=3.0 Hz), 2.15 (1H, m), 1.51, 1.46 (each 9H, each s), 1.01-0.86 (18H, m), 0.21, 0.17 (each 3H, each s); FAB-LRMS m/z 694 (MH$^+$).

3'-O-Dimethylthexylsilyl-5'-O-(L-valyl)-2'-cyano-2'-deoxy-1-β-D-arabinofuranosylcytosine bis(trifluoroacetate) (31)

Compound 31b (1.00 g, 1.44 mmol) was dissolved in dichloromethane (10 mL). Under cooling with ice, trifluoroacetic acid (10 mL) was added thereto, and the resultant mixture was stirred for 3 hours. The reaction mixture was diluted with ethanol, and concentrated under reduced pressure. The residue was co-boiled with ethanol several times, followed by purification through silica gel column chromatography (5 to 15% methanol/chloroform), whereby the Compound 31 was obtained as a white solid (812 mg, 78%).

$^1$H-NMR (CDCl$_3$) δ 8.41 (2H, br s), 7.93 (1H, br s), 7.75 (1H, br s), 7.69 (1H, d, J=7.6 Hz), 6.19 (1H, d, J=7.9 Hz), 5.88 (1H, d, J=7.6 Hz), 4.75 (1H, t, J=7.6 Hz), 4.54 (1H, m), 4.38 (1H, m), 3.99 (3H, m), 2.17 (1H, m), 1.59 (1H, m), 0.95 (6H, m), 0.85 (12H, m), 0.21, 0.18 (each 3H, each s); FAB-LRMS m/z 494 (MH-2TFA)$^+$. Anal. Calcd for C$_{27}$H$_{41}$F$_6$N$_5$O$_9$Si: C, 44.93; H, 5.73; N, 9.70. Found: C, 44.90; H, 6.18; N, 9.99; mp 118-120° C.

EXAMPLE 32

4-N-(tert-Butoxycarbonyl)-5'-O-[N-(tert-butoxycarbonyl)-L-valyl]-3'-O-(tert-butyldimethylsilyl)-2'-cyano-2'-deoxy-1-β-D-arabinofuranosylcytosine (32a)

Compound 24c (700 mg, 1.50 mmol) was dissolved in dichloromethane (20 mL), and Boc-l-Val-OH (652 mg, 3.00 mmol), EDC (575 mg, 3.00 mmol), and DMAP (9 mg, 0.08 mmol) were added thereto, and the resultant mixture was stirred under nitrogen at 0° C. for 3 hours. The reaction mixture was partitioned between ethyl acetate and water, and the formed organic layer was sequentially washed with water and saturated brine, followed by drying over sodium sulfate anhydrate. After removal of solvent, the residue was purified through silica gel column chromatography (0 to 2% methanol/chloroform), whereby the Compound 32a was obtained as a white foam (1.02 g, quant.).

$^1$H-NMR (CDCl$_3$) δ 7.98 (1H, d, J=7.9 Hz), 7.38 (2H, m), 6.23 (1H, d, J=5.9 Hz), 5.01 (1H, d, J=8.4 Hz), 4.56 (2H, m), 4.34-4.14 (3H, m), 3.73 (1H, dd, J=5.9 Hz, J=2.8 Hz), 2.15 (1H, m), 1.52, 1.46 (each 9H, each s), 1.01-0.91 (15H, m), 0.18, 0.14 (each 3H, each s); FAB-LRMS m/z 666 (MH$^+$)

5'-O-(L-Valyl)-3'-O-(tert-butyldimethylsilyl)-2'-cyano-2'-deoxy-1-β-D-arabinofuranosylcytosine bis(trifluoroacetate) (32)

Compound 32a (960 mg, 1.44 mmol) was dissolved in dichloromethane (10 mL). Under cooling with ice, trifluoroacetic acid (10 mL) was added thereto, and the resultant mixture was stirred for 90 minutes. The reaction mixture was diluted with ethanol, and concentrated under reduced pressure. The residue was co-boiled with ethanol several times, followed by purification through silica gel column chromatography (5 to 15% methanol/chloroform), whereby the Compound 32 was obtained as a white solid (682 mg, 68%).

$^1$H-NMR (DMSO) δ 8.43 (2H, br s), 7.79 (1H, br s), 7.67 (2H, m), 6.18 (1H, d, J=8.2 Hz), 5.86 (1H, d, J=7.6 Hz), 4.75 (1H, m), 4.53 (1H, m), 4.38 (1H, dd, J=6.6 Hz, J=12.2 Hz), 3.99 (3H, m), 2.17 (1H, m), 0.95 (6H, t, J=7.3 Hz), 0.88 (9H, s), 0.17, 0.15 (each 3H, each s); FAB-LRMS m/z 466 (MH-2TFA)$^+$; Anal. Calcd for C$_{25}$H$_{37}$F$_6$N$_5$O$_9$Si.0.3H$_2$O: C, 42.95; H, 5.42; N, 10.02. Found: C, 42.86; H, 5.89; N, 10.14; mp 118-120° C.

EXAMPLE 33

5'-O-(Di-tert-butylmethylsilyl)-2'-cyano-2'-deoxy-1-β-D-arabinofuranosylcytosine (33)

Di-tert-butylmethylsilane (2.00 g, 12.6 mmol) was dissolved in dichloromethane (25 mL), and N-bromosuccinimide (2.14 g, 12.0 mmol) was added thereto at 0° C., and the resultant mixture was stirred at room temperature for one hour and 30 minutes. The solvent was removed under reduced pressure, and the residue was dissolved in DMF (6.3 mL). CNDAC hydrochloride (1.45 g, 5.04 mmol) and imidazole (2.06 g, 30.2 mmol) were added thereto, and the resultant mixture was stirred at room temperature overnight. The reaction mixture was partitioned between ethyl acetate and water, and the formed organic layer was washed with saturated brine, followed by drying over sodium sulfate anhydrate. After removal of solvent, the residue was purified through neutral silica gel column chromatography (0 to 9% methanol/chloroform), followed by crystallization from methanol, whereby the Compound 34 was obtained as a white solid (350 mg, 17%).

$^1$H-NMR (DMSO-d$_6$) δ 7.72 (1H, d, J=7.3 Hz), 7.38 (2H, br d), 6.28 (1H, d, J=5.9 Hz), 6.21 (1H, d, J=7.3 Hz), 5.74 (1H, d, J=7.3 Hz), 4.44 (1H, dd, J=13.4 Hz, J=7.8 Hz), 3.98 (1H, m) 3.89-3.81 (3H, m), 0.98 (18H, s), 0.11 (3H, s); FAB-LRMS m/z 409 (MH$^+$); Anal. Calcd for C$_{19}$H$_{32}$N$_4$O$_4$Si: C, 55.86; H, 7.89; N, 13.71.

Found: C, 55.85; H, 7.91; N, 14.11.

EXAMPLE 34, 35 tert-Amyldiethylsilane (34a)

Magnesium (2.43 g, 100 mmol) and iodine (catalytic amount) were added to THF (20 mL), and tert-amyl chloride (12.3 mL, 100 mmol) was added dropwise thereto in a nitrogen atmosphere for 20 minutes, followed by stirring at room temperature for 1 hour. After termination of exothermic reaction, the resultant mixture was further stirred at 50° C. for 5 hours, to thereby prepare tert-amylmagnesium chloride THF solution.

Trichlorosilane (9.70 mL, 96.1 mmol) was dissolved in THF (100 mL), and ethylmagnesium chloride THF solution (0.93M, 200 mL, 186 mmol) was added dropwise thereto in a nitrogen atmosphere at 0° C., followed by stirring at room temperature for 1 hour. Cuprous bromide (286 mg, 2.00 mmol) was added to the resultant mixture, and the above-prepared tert-amylmagnesium chloride THF solution (100 mL) was added dropwise thereto for 30 minutes, and the resultant mixture was stirred at 70° C. for 8 hours. The reaction mixture was left to cool, and saturated aqueous ammonium chloride and n-pentane were added thereto. The formed organic layer was washed three times with water and once with saturated brine, followed by drying over sodium sulfate anhydrate. The solvent was removed, followed by purification through distillation under reduced pressure, whereby the Compound 34a was obtained as a colorless liquid (boiling point; 30 mmHg, 95° C. fraction, 4.53 g, 30%).

$^1$H-NMR (CDCl$_3$) δ 3.47 (1H, m), 1.32 (2H, m), 1.04-0.93 (6H, m), 0.91 (6H, s), 0.86 (3H, t, J=7.6 Hz), 0.61 (4H, m).

5'-O-(tert-Amyldiethylsilyl)-2'-cyano-2'-deoxy-1-β-D-arabinofuranosylcytosine (34)

3',5'-Bis-O-(tert-amyldiethylsilyl)-2'-cyano-2'-deoxy-1-β-D-arabinofuranosylcytosine (35)

Compound 34a (2.00 g, 12.6 mmol) was dissolved in dichloromethane (25 mL), and N-bromosuccinimide (2.90 g, 12.3 mmol) was added thereto at 0° C., and the resultant mixture was stirred at room temperature for 1 hour. The solvent was removed under reduced pressure, and the residue was dissolved in DMF (5 mL). CNDAC hydrochloride (1.11 g, 3.87 mmol) and imidazole (1.72 g, 32.0 mmol) were added thereto, and the resultant mixture was stirred at room temperature overnight. The reaction mixture was partitioned between ethyl acetate and water, and the formed organic layer was washed with saturated brine, followed by drying over sodium sulfate anhydrate. After removal of solvent, the residue was purified through neutral silica gel column chromatography (0-9% methanol/chloroform), whereby the Compound 34 (494 mg, 31%) and the Compound 35 (600 mg, 27%) were obtained, both assuming a white foam.

Compound 34
$^1$H-NMR (DMSO-$d_6$) δ 7.74 (1H, d, J=7.6 Hz), 7.27 (2H, br d), 6.26 (1H, m), 6.20 (1H, d, J=7.6 Hz), 5.73 (1H, d, J=7.3 Hz), 4.34 (1H, m), 3.95 (1H, m) 3.86-3.78 (3H, m), 1.34 (2H, q, J=7.8 Hz), 1.06-0.97 (6H, m), 0.89 (6H, s), 0.83 (3H, t, J=7.8 Hz), 0.69 (4H, q, J=7.8 Hz); FAB-LRMS (negative) m/z 407 (M-H)$^-$.

Compound 35
$^1$H-NMR (DMSO-$d_6$) δ 7.63 (1H, d, J=7.3 Hz), 7.29 (2H, br s), 6.22 (1H, d, J=7.3 Hz), 5.76 (1H, d, J=7.3 Hz), 4.66 (1H, t, J=6.6 Hz), 4.33 (1H, t, J=4.9 Hz), 3.91-3.85 (3H, m), 1.36-0.53 (42H, m); FAB-LRMS m/z 565 (MH$^+$).

EXAMPLE 36, 37 tert-Butyldiisobutylsilane (36a)

Diisobutylchlorosilane (18.0 mL, 100 mmol) was dissolved in THF (100 mL), and tert-butyl magnesium chloride THF solution (10M, 100 mL) was added dropwise thereto under nitrogen for 30 minutes. Cuprous bromide (286 mg, 2.00 mmol) was added to the resultant mixture, followed by stirring at 70° C. for 8 hours. The reaction mixture was left to cool, and saturated aqueous ammonium chloride and n-pentane were added thereto. The formed organic layer was washed three times with water and once with saturated brine, and the thus-washed layer was dried over sodium sulfate anhydrate. The solvent was removed, followed by purification through distillation under reduced pressure, whereby the Compound 36a was obtained as a colorless liquid (boiling point; 27 mmHg, 100° C. fraction, 13.6 g, 68%).

$^1$H-NMR (CDCl$_3$) δ 3.75 (1H, bs), 1.80 (1H, m), 0.96 (12H, d, J=5.4 Hz), 0.91 (9H, s), 0.54 (4H, m).

5'-O-(tert-Butyldiisobutylsilyl)-2'-cyano-2'-deoxy-1-β-D-arabinofuranosylcytosine (36)

3',5'-Bis-O-(tert-butyldiisobutylsilyl)-2'-cyano-2'-deoxy-1-β-D-arabinofuranosylcytosine (37)

Compound 36a (1.39 g, 6.92 mmol) was dissolved in dichloromethane (13.8 mL), and N-bromosuccinimide (1.20 g, 6.75 mmol) was added thereto at 0° C., and the resultant mixture was stirred at room temperature for 1 hour. The solvent was removed under reduced pressure, and the residue was dissolved in DMF (2.3 mL). CNDAC hydrochloride (500 mg, 1.73 mmol) and imidazole (770 mg, 11.3 mmol) were added thereto, the resultant mixture was stirred at room temperature overnight. The reaction mixture was partitioned between ethyl acetate and water, and the formed organic layer was washed with saturated brine, followed by drying over sodium sulfate anhydrate. After removal of solvent, the residue was purified through neutral silica gel column chromatography (0 to 9% methanol/chloroform), whereby the Compound 36 (425 mg, 0.94 mmol, 54%) and the Compound 37 (450 mg, 40%) were obtained, both assuming a white foam.

Compound 36
$^1$H-NMR (DMSO-$d_6$) δ 7.68 (1H, d, J=7.3 Hz), 7.27 (2H, br d), 6.23 (1H, d, J=5.9 Hz), 6.18 (1H, d, J=7.3 Hz), 5.74 (1H, d, J=7.6 Hz), 4.40 (1H, dd, J=7.6 Hz, 13.2 Hz), 3.96 (1H, dd, J=3.9 Hz, 11.7 Hz), 3.85-3.78 (3H, m), 1.90-1.83 (2H, m), 0.96 (12H, m), 0.91 (9H, s), 0.86-0.62 (4H, m); FAB-LRMS (negative) m/z 449 (M-H)$^-$.

Compound 37
$^1$H-NMR (DMSO-$d_6$) δ 7.54 (1H, d, J=7.3 Hz), 7.25 (2H, br d), 6.09 (1H, d, J=7.3 Hz), 5.69 (1H, d, J=7.6 Hz), 4.63 (1H, m), 3.85-3.80 (4H, m), 1.79 (4H, m), 0.90 (12H, d, J=6.8 Hz), 0.88 (9H, s), 0.63 (8H, m); FAB-LRMS (negative) m/z 647 (M-H)$^-$.

EXAMPLE 38

Diethyl(3-methylpentan-3-yl)silane (38a)

The procedure of synthesizing Compound 34a was repeated, except that 3-methylpentan-3-ylmaganesium chloride THF solution (100 mL), which had been prepared from magnesium (2.43 g, 100 mmol) and 3-chloro-3-methylpentane (13.6 mL, 100 mmol); trichlorosilane (10.0 mL, 99.1 mmol); and ethylmagnesium chloride THF solution (0.93M, 200 mL, 190 mmol) were employed, whereby the Compound 38a was obtained as a colorless liquid (boiling point; 39 to 42 mmHg, 94 to 97° C. fraction, 8.86 g, 51%).

$^1$H-NMR (CDCl$_3$) δ 3.52 (1H, bs), 1.37 (4H, m), 1.04-0.97 (9H, m), 0.90-0.84 (6H, m), 0.62 (4H, m).

5'-O-[Diethyl(3-methylpentan-3-yl)silyl]-2'-cyano-2'-deoxy-1-β-D-arabinofuranosylcytosine (38)

The procedure of synthesizing Compound 34 was repeated, except that Compound 38a (3.44 g, 20.0 mmol), N-bromosuccinimide (3.38 g, 19.0 mmol), CNDAC hydrochloride (2.30 g, 7.97 mmol), and imidazole (1.30 g, 19.0 mmol) were employed, whereby the Compound 38 was obtained as a white foam (300 mg, 0.71 mmol, 9%).

$^1$H-NMR (DMSO-$d_6$) δ 7.72 (1H, d, J=7.6 Hz), 7.26 (2H, br d), 6.25 (1H, d, J=5.6 Hz), 6.19 (1H, d, J=7.6 Hz), 5.74 (1H, d, J=7.3 Hz), 4.30 (1H, dd, J=7.6 Hz, J=13.4 Hz), 3.96 (1H, dd, J=2.0 Hz, J=11.7 Hz), 3.87-3.77 (3H, m), 1.47-1.31 (4H, m), 0.99 (6H, t, J=7.8 Hz), 0.86 (3H, s), 0.81 (6H, t, J=7.3 Hz), 0.69 (4H, m); FAB-LRMS m/z 423 (MH$^+$); Anal. Calcd for $C_{20}H_{34}N_4O_4Si$: C, 56.84; H, 8.11; N, 13.26. Found: C, 55.61; H, 8.15; N, 13.50.

EXAMPLE 39

3'-O-(tert-Amyldiethylsilyl)-2'-cyano-2'-deoxy-1-β-D-arabinofuranosylcytosine (39)

Compound 35 (600 mg, 1.06 mmol) was dissolved in methanol (1.8 mL), and methanesulfonic acid (137 μL) was added thereto, and the resultant mixture was stirred at room temperature for 2 hours. Subsequently, saturated aqueous sodium hydrogencarbonate and ethyl acetate were added to the reaction mixture, and the formed organic layer was sequentially washed with water and saturated brine, followed by drying over sodium sulfate anhydrate. After removal of solvent, the residue was purified through neutral silica gel column chromatography (9% methanol/chloroform), whereby the Compound 39 was obtained as a white foam (147 mg, 34%).

$^1$H-NMR (DMSO-$d_6$) δ 7.79 (1H, d, J=7.6 Hz), 7.27 (2H, br d), 6.16 (1H, d, J=7.6 Hz), 5.77 (1H, d, J=7.6 Hz), 5.21 (1H, m), 4.65 (1H, t, J=6.3 Hz), 3.85-3.59 (3H, m), 3.60 (1H, m), 1.34 (2H, q, J=7.6 Hz), 1.00 (6H, m), 0.88 (6H, s), 0.82 (3H, t, J=7.6 Hz), 0.73 (4H, m); FAB-LRMS (negative) m/z 407 (M-H)$^-$.

EXAMPLE 40

Isobutyldiisopropylsilane (40a)

Diisopropylchlorosilane (16.4 mL, 96.1 mmol) was dissolved in THF (100 mL), and isobutylmagnesium bromide THF solution (1.0M, 100 mL) was added dropwise thereto under nitrogen for 30 minutes. Subsequently, cuprous bromide (286 mg, 2.00 mmol) was added to the resultant mixture, followed by stirring at 70° C. overnight. The reaction mixture was left to cool, and saturated aqueous ammonium chloride and n-pentane were added thereto. The formed organic layer was washed three times with water and once with saturated brine, followed by drying over sodium sulfate anhydrate. The solvent was removed, followed by purification through distillation under reduced pressure, whereby the Compound 40a was obtained as a colorless liquid (boiling point; 70 mmHg, 102 to 106° C. fraction, 8.26 g, 50%).

$^1$H-NMR (CDCl$_3$) δ 3.49 (1H, m), 1.80 (1H, m), 1.05 (12H, m), 0.98 (6H, m), 0.88 (2H, m), 0.56 (2H, m).

3',5'-Bis-O-isobutyldiisopropylsilyl-2'-cyano-2'-deoxy-1-β-D-arabinofuranosylcytosine (40)

Compound 40a (1.53 g, 8.90 mmol) was dissolved in dichloromethane (25 mL), and N-bromosuccinimide (1.54 g, 8.68 mmol) was added thereto at 0° C., and the resultant mixture was stirred at room temperature for 30 minutes. After the solvent was removed under reduced pressure, the residue was dissolved in DMF (2.3 mL), and CNDAC hydrochloride (500 mg, 1.73 mmol) and imidazole (770 mg, 11.3 mmol) were added thereto, and the resultant mixture was stirred at room temperature for 7 hours. The reaction mixture was partitioned between ethyl acetate and water, and the formed organic layer was washed with saturated brine, followed by drying over sodium sulfate anhydrate. After removal of solvent, the residue was purified through neutral silica gel column chromatography (5% methanol/chloroform), whereby the Compound 40 was obtained as a white foam (910 mg, 88%).

$^1$H-NMR (DMSO-$d_6$) δ 7.65 (1H, d, J=7.6 Hz), 7.29 (2H, br d), 6.22 (1H, d, J=7.6 Hz), 5.75 (1H, d, J=7.6 Hz), 4.68 (1H, m), 3.98-3.84 (4H, m), 1.84 (2H, m), 1.02 (28H, m), 0.95 (12H, d, J=6.6 Hz), 0.66 (4H, m); FAB-LRMS m/z 593 (MH$^+$).

EXAMPLE 41

3'-O-Isobutyldiisopropylsilyl-2'-cyano-2'-deoxy-1-β-D-arabinofuranosylcytosine (41)

The procedure of synthesizing Compound 39 was repeated, except that Compound 40 (400 mg, 0.675 mmol) and methanesulfonic acid (87 μL, 1.3 mmol) were employed, whereby the Compound 41 was obtained as a white foam (263 mg, 93%).

$^1$H-NMR (DMSO-$d_6$) δ 7.79 (1H, d, J=7.6 Hz), 7.27 (2H, br d), 6.15 (1H, d, J=7.6 Hz), 5.77 (1H, d, J=7.6 Hz), 5.22 (1H, m), 4.68 (1H, t, J=6.1 Hz), 3.83 (2H, m), 3.74 (1H, m) 3.58 (1H, m), 1.84 (1H, m), 1.02-0.91 (20H, m), 0.68 (2H, m); FAB-LRMS (negative) m/z 421 (M-H)$^-$.

EXAMPLE 42

Diethyl(2-methylpentan-2-yl)silane (42a)

The procedure of synthesizing Compound 34a was repeated, except that 2-methylpentan-2-ylmagnesium chloride THF solution (100 mL), which had been prepared from magnesium (2.43 g, 100 mmol) and 2-chloro-2-methylpentane (12.0 g, 99.0 mmol); trichlorosilane (9.70 mL, 96.1 mmol); and ethylmagnesium chloride THF solution (0.93M, 200 mL, 1.86 mmol) were employed, whereby the Compound 42a was obtained as a colorless liquid (boiling point; 40 mmHg, 100 to 103° C. fraction, 6.62 g, 40%).

$^1$H-NMR (CDCl$_3$) δ 3.47 (1H, m), 1.32-1.21 (4H, m), 0.96 (6H, t, J=8.1 Hz), 0.92 (6H, s), 0.88 (3H, t, J=6.5 Hz), 0.66-0.56 (4H, m).

3',5'-Bis-O-[diethyl(2-methylpentan-2-yl)silyl]-2'-cyano-2'-deoxy-1-β-D-arabinofuranosylcytosine (42)

The procedure of synthesizing Compound 40 was repeated, except that Compound 42a (2.76 g, 16.0 mmol), N-bromosuccinimide (2.77 g, 15.6 mmol), CNDAC hydrochloride (1.41 g, 4.90 mmol), and imidazole (2.18 g, 32.0 mmol) were employed, whereby the Compound 42 was obtained as a white foam (1.67 g, 57%).

$^1$H-NMR (DMSO-$d_6$) δ 7.62 (1H, d, J=7.3 Hz), 7.31 (2H, m), 6.22 (1H, d, J=7.3 Hz), 5.76 (1H, d, J=7.6 Hz), 4.66 (1H, m), 3.98-3.84 (4H, m), 1.26 (8H, m), 1.06-0.84 (30H, m), 0.63 (8H, m); FAB-LRMS m/z 593 (MH$^+$).

EXAMPLE 43

3'-O-[Diethyl(2-methylpentan-2-yl)silyl]-2'-cyano-2'-deoxy-1-β-D-arabinofuranosylcytosine (43)

The procedure of synthesizing Compound 39 was repeated, except that Compound 42(360 mg, 0.607 mmol) and methanesulfonic acid (80 μL, 1.2 mmol) were employed, whereby the Compound 43 was obtained as a white foam (55 mg, 11%).

$^1$H-NMR (DMSO-$d_6$) δ 7.71 (1H, d, J=7.3 Hz), 7.27 (2H, br d), 6.17 (1H, d, J=7.3 Hz), 5.78 (1H, d, J=7.3 Hz), 5.19 (1H, m), 4.66 (1H, t, J=6.3 Hz), 3.85-3.54 (4H, m), 1.28 (4H, m), 1.03-0.97 (6H, m), 0.88 (6H, s), 0.82 (3H, t, J=7.6 Hz), 0.73 (4H, m); FAB-LRMS m/z 423 (MH$^+$).

EXAMPLE 44

Cyclopropyldiisopropylsilane (44a)

The procedure of synthesizing Compound 40a was repeated, except that diisopropylchlorosilane (4.10 mL, 96.0 mmol) and cyclopropylmagnesium bromide THF solution (1.0M, 100 mL) were employed, whereby the Compound 44a was obtained as a colorless liquid (boiling point; 35 mmHg, 86 to 89° C. fraction, 1.84 g, 50%).

$^1$H-NMR (CDCl$_3$) δ 3.01 (1H, m), 1.07 (14H, m), 0.62 (2H, m), 0.28 (2H, m), −0.46 (1H, m).

3',5'-Bis-O-cyclopropyldiisopropylsilyl-2'-cyano-2'-deoxy-1-β-D-arabinofuranosylcytosine (44)

The procedure of synthesizing Compound 40 was repeated, except that cyclopropyldiisopropylsilane (1.05 g, 6.92 mmol), N-bromosuccinimide (1.20 g, 6.75 mmol), CNDAC hydrochloride (500 mg, 1.73 mmol), and imidazole (770 mg, 11.3 mmol) were employed, whereby the Compound 44 was obtained as a pale yellow liquid (880 mg, 91%).

$^1$H-NMR (CDCl$_3$) δ 7.76 (1H, d, J=7.6 Hz), 6.26 (1H, d, J=5.9 Hz), 5.74 (1H, d, J=7.6 Hz), 4.03 (1H, m), 3.68 (1H, t, J=2.9 Hz), 1.04 (28H, m), 0.67 (4H, m), 0.44 (4H, m), −0.38 (2H, m); FAB-LRMS m/z 561 (MH$^+$).

EXAMPLE 45

3'-O-Cyclopropyldiisopropylsilyl-2'-cyano-2'-deoxy-1-β-D-arabinofuranosylcytosine (45)

The procedure of synthesizing Compound 39 was repeated, except that Compound 44 (880 mg, 1.57 mmol) and methanesulfonic acid (203 μL, 3.14 mmol) were employed, whereby the Compound 45 was obtained as a white foam (240 mg, 38%).

$^1$H-NMR (DMSO-d$_6$) δ 7.79 (1H, d, J=7.3 Hz), 7.26 (2H, br d), 6.15 (1H, d, J=7.3 Hz), 5.77 (1H, d, J=7.6 Hz), 5.20 (1H, m), 4.75 (1H, m), 3.85-3.73 (3H, m), 3.61 (1H, m), 1.01 (14H, m), 0.63 (2H, m), 0.39 (2H, m), −0.35 (1H, m); FAB-LRMS (negative) m/z 405 (M-H)$^-$; Anal. Calcd for C$_{19}$H$_{30}$N$_4$O$_4$Si: C, 56.13; H, 7.44; N, 13.78. Found: C, 55.41; H, 7.37; N, 13.95.

EXAMPLE 46

3'-O-(tert-Butyldiisobutylsilyl)-2'-cyano-2'-deoxy-1-β-D-arabinofuranosylcytosine (46)

The procedure of synthesizing Compound 39 was repeated, except that Compound 37 (250 mg, 0.39 mmol) and methanesulfonic acid (25 μL, 0.39 mmol) were employed, whereby the Compound 46 was obtained as a white foam (50 mg, 29%).

$^1$H-NMR (DMSO-d$_6$) δ 7.79 (1H, d, J=7.3 Hz), 7.27 (2H, br d), 6.13 (1H, d, J=7.3 Hz), 5.77 (1H, d, J=7.6 Hz), 5.22 (1H, m), 4.70 (1H, t, J=5.9 Hz), 3.86-3.79 (2H, m), 3.74 (1H, dd, J=4.9 Hz, J=12.3 Hz), 3.61 (1H, dd, J=4.2 Hz, J=12.3 Hz), 1.92-1.82 (2H, m), 0.98 (12H, m), 0.91 (9H, s), 0.86-0.62 (4H, m); FAB-LRMS (negative) m/z 449 (M-H)$^-$.

EXAMPLE 47 n-Butyldiisopropylsilane (47a)

Diisopropylchlorosilane (13.1 mL, 76.8 mmol) was dissolved in THF (75 mL), and n-butylmagnesium chloride THF solution (0.84M, 100 mL, 84 mmol) was added dropwise thereto in a nitrogen atmosphere for 10 minutes. Subsequently, cuprous bromide (286 mg, 2.00 mmol) was added to the resultant mixture, followed by stirring at 65° C. for 8 hours. The reaction mixture was left to cool, and saturated aqueous ammonium chloride and n-pentane were added thereto. The formed organic layer was washed three times with water and once with saturated brine, and the thus-washed layer was dried over sodium sulfate anhydrate. The solvent was removed, followed by purification through distillation under reduced pressure, whereby the Compound 47a was obtained as a colorless liquid (boiling point; 50 mmHg, 93.2 to 95.5° C. fraction, 8.43 g, 64%).

$^1$H-NMR (CDCl$_3$) δ 3.41 (1H, m), 1.41-1.30 (4H, m), 1.06-1.01 (14H, m), 0.94-0.86 (3H, m), 0.64-0.57 (2H, m).

3',5'-Bis-O—(n-butyldiisopropylsilyl)-2'-cyano-2'-deoxy-1-β-D-arabinofuranosylcytosine (47)

Compound 47a (2.17 g, 12.6 mmol) was dissolved in dichloromethane (25 mL), and N-bromosuccinimide (2.19 g, 12.3 mmol) was added thereto at 0° C., and the resultant mixture was stirred at room temperature for 30 minutes. After removal of solvent under reduced pressure, the residue was dissolved in DMF (5 mL). Subsequently, CNDAC hydrochloride (1.11 g, 3.84 mmol) and imidazole (1.72 g, 25.2 mmol) were added thereto, and the resultant mixture was stirred at 60° C. for 7 hours. The reaction mixture was partitioned between ethyl acetate and water, and the formed organic layer was washed with saturated brine, followed by drying over sodium sulfate anhydrate. After removal of solvent, the residue was purified through silica gel column chromatography (0 to 9% methanol/chloroform), whereby the Compound 47 was obtained as a white foam (522 mg, 23%).

$^1$H-NMR (DMSO-d$_6$) 7.60 (1H, d, J=7.3 Hz), 7.23 (2H, br s), 6.18 (1H, d, J=7.3 Hz), 5.69 (1H, d, J=7.3 Hz), 4.60 (1H, t, J=7.8 Hz), 3.93-3.64 (4H, m), 1.29-1.24 (8H, m) 0.97-0.95 (28H, m), 0.81-0.79 (6H, m), 0.71-0.62 (4H, m); FAB-LRMS m/z 593 (MH$^+$).

EXAMPLE 48

3'-O-(n-Butyldiisopropylsilyl)-2'-cyano-2'-deoxy-1-β-D-arabinofuranosylcytosine (48)

Compound 47 (522 mg, 0.880 mmol) was dissolved in methanol (1.5 mL), and methanesulfonic acid (0.10 mL) was added thereto, the resultant mixture was stirred at room temperature for 30 minutes. Subsequently, saturated aqueous sodium hydrogencarbonate and ethyl acetate were added to the reaction mixture, and the organic layer was sequentially washed with water and saturated brine, followed by drying over sodium sulfate anhydrate. After removal of solvent, the residue was purified through neutral silica gel column chromatography (11% methanol/chloroform), whereby the Compound 48 was obtained as a white foam (179 mg, 48%).

$^1$H-NMR (DMSO-d$_6$) δ 7.79 (1H, d, J=7.4 Hz), 7.26 (2H, br d), 6.16 (1H, d, J=7.3 Hz), 5.77 (1H, d, J=7.4 Hz), 5.21 (1H, br s), 4.65 (1H, t, J=6.4 Hz), 3.86-3.78 (3H, m), 3.73-3.56 (1H, m), 1.01 (14H, m), 0.89-0.84 (3H, m), 0.74-0.69 (2H, m); FAB-LRMS m/z 423 (MH$^+$).

EXAMPLE 49

Diisopropyl-n-propylsilane (49a)

The procedure of synthesizing Compound 47a was repeated, except that n-propylmagnesium bromide THF solution (1.04M, 100 mL, 104 mmol) was employed, whereby the Compound 49a was obtained as a colorless liquid (boiling point; 60 mmHg, 99.5 to 103.0° C. fraction, 9.38 g, 62%).

$^1$H-NMR (CDCl$_3$) δ 3.43 (1H, br s), 1.53-1.40 (2H, m), 1.32-0.91 (14H, m), 0.64-0.57 (2H, m).

3',5'-Bis-O-(diisopropyl-n-propylsilyl)-2'-cyano-2'-deoxy-1-β-D-arabinofuranosylcytosine (49)

The procedure of synthesizing Compound 47 was repeated, except that CNDAC hydrochloride (2.22 g, 7.69 mmol) and Compound 49a (3.99 g, 25.2 mmol) were employed, whereby the Compound 49 was obtained as a white foam (1.82 g, 42%).

$^1$H-NMR (DMSO-d$_6$) δ 7.60 (1H, d, J=7.6 Hz), 7.23 (2H, br s), 6.18 (1H, d, J=7.4 Hz), 5.69 (1H, d, J=7.6 Hz), 4.59 (1H, t, J=7.3 Hz), 3.96-3.87 (2H, m), 3.79-3.73 (2H, m), 1.40-1.17 (4H, m), 0.99-0.86 (28H, m), 0.68-0.57 (4H, m); FAB-LRMS m/z 565 (MH$^+$).

EXAMPLE 50

3'-O-(Diisopropyl-n-propylsilyl)-2'-cyano-2'-deoxy-1-β-D-arabinofuranosylcytosine (50)

The procedure of synthesizing Compound 48 was repeated, except that Compound 49 (1.17 g, 2.07 mmol) was employed, whereby the Compound 50 was obtained as a white foam (381 mg, 45%).

$^1$H-NMR (DMSO-d$_6$) δ 7.79 (1H, d, J=7.4 Hz), 7.26 (2H, br d), 6.16 (1H, d, J=7.3 Hz), 5.77 (1H, d, J=7.4 Hz), 5.20 (1H, t, J=5.12), 4.65 (1H, t, J=6.4 Hz), 3.86-3.56 (3H, m), 3.34-3.27 (1H, m), 1.46-1.34 (2H, m) 1.04-0.93 (17H, m), 0.74-0.68 (2H, m); FAB-LRMS m/z 409 (MH$^+$). Anal. Calcd for C$_{19}$H$_{32}$N$_4$O$_4$Si: C, 55.86; H, 7.89; N, 13.71. Found: C, 55.44; H, 7.84; N, 13.51.

EXAMPLE 51

Diisopropyl(2,2-dimethylpropyl)silane (51a)

Magnesium (2.43 g, 100 mmol) and iodine (catalytic amount) were added to THF (100 mL), and 1-bromo-2,2-dimethylpropane (10.7 mL, 100 mmol) was added dropwise thereto for 20 minutes, followed by stirring at room temperature for 1 hour. After termination of exothermic reaction, the resultant mixture was further stirred at 50° C. for 5 hours, whereby 2,2-dimethylpropylmagnesium bromide THF solution was prepared. The procedure of synthesizing Compound 47a was repeated, except that the thus-prepared mixture was employed, whereby the Compound 51a was obtained as a colorless liquid (boiling point; 40 mmHg, 120.0 to 122.5° C. fraction, 7.65 g, 45%).

$^1$H-NMR (CDCl$_3$) δ 3.60 (1H, br s), 1.03-0.85 (23H, m), 0.67-0.63 (2H, m).

3',5'-Bis-O-[diisopropyl(2,2-dimethylpropyl)silyl]-2'-cyano-2'-deoxy-1-β-D-arabinofuranosylcytosine (51)

The procedure of synthesizing Compound 47 was repeated, except that CNDAC hydrochloride (550 mg, 1.92 mmol) and Compound 51a (2.35 g, 12.6 mmol) were employed, whereby the Compound 51 was obtained as a white foam (532 mg, 45%).

$^1$H-NMR (CDCl$_3$) δ 7.73 (1H, d, J=7.4 Hz), 6.22 (1H, d, J=5.6 Hz), 5.73 (1H, d, J=7.4 Hz), 4.77 (1H, br s), 4.11-3.91 (3H, m), 3.72-3.69 (1H, m), 1.12-0.98 (46H, m), 0.80-0.78 (4H, m); FAB-LRMS m/z 622 (MH$^+$).

EXAMPLE 52

3'-O-[Diisopropyl(2,2-dimethylpropyl)silyl]-2'-cyano-2'-deoxy-1-β-D-arabinofuranosylcytosine(52)

The procedure of synthesizing Compound 48 was repeated, except that Compound 51 (512 mg, 0.824 mmol) was employed, whereby the Compound 52 was obtained as a white foam (166 mg, 46%).

$^1$H-NMR (CDCl$_3$) δ 7.78 (1H, d, J=7.4 Hz), 6.23 (1H, d, J=6.3 Hz), 5.78 (1H, d, J=7.4 Hz), 4.04-4.00 (2H, m), 3.85-3.79 (1H, m), 3.70-3.66 (1H, m), 1.10-1.00 (23H, m), 0.57 (2H, br s); FAB-LRMS m/z 437 (MH$^+$). Anal. Calcd for C$_{21}$H$_{36}$N$_4$O$_4$Si: C, 57.77; H, 8.31; N, 12.83. Found: C, 57.77; H, 8.35; N, 12.61.

EXAMPLE 53

(3-Methylbutyl)diisopropylsilane (53a)

The procedure of synthesizing Compound 51a was repeated, except that 1-bromo-3-methylbutane (12.6 mL, 100 mmol) was employed, whereby the Compound 53a was obtained as a colorless liquid (12.6 g, 73%).

$^1$H-NMR (CDCl$_3$) δ 3.41 (1H, br s), 1.53-1.41 (1H, m), 1.30-1.21 (2H, m), 1.10-0.91 (14H, m), 0.90-0.82 (6H, m), 0.61-0.57 (2H, m).

3',5'-Bis-O-[(3-methylbutyl)diisopropylsilyl]-2'-cyano-2'-deoxy-1-β-D-arabinofuranosylcytosine (53)

The procedure of synthesizing Compound 47 was repeated, except that CNDAC hydrochloride (520 mg, 1.80 mmol) and Compound 53a (2.35 g, 12.6 mmol) were employed, whereby the Compound 53 was obtained as a white foam (515 mg, 46%).

$^1$H-NMR (CDCl$_3$) δ 7.78 (1H, d, J=7.4 Hz), 6.30 (1H, d, J=5.9 Hz), 5.72 (1H, d, J=7.4 Hz), 4.76 (1H, t, J=3.7 Hz), 4.01-3.86 (3H, m), 3.64-3.60 (1H, m), 1.52-1.49 (2H, m), 1.47-1.20 (4H, m), 1.06-1.00 (28H, m), 0.89 (12H, d, J=5.1), 0.73-0.65 (4H, m); FAB-LRMS m/z 622 (MH$^+$).

EXAMPLE 54

3'-O-[(3-Methylbutyl)diisopropylsilyl]-2'-cyano-2'-deoxy-1-β-D-arabinofuranosylcytosine (54)

The procedure of synthesizing Compound 48 was repeated, except that Compound 53 (500 mg, 0.805 mmol) was employed, whereby the Compound 54 was obtained as a white foam (166 mg, 50%).

$^1$H-NMR (DMSO-d$_6$) 7.79 (1H, d, J=7.4 Hz), 7.28 (2H, br d), 6.25 (1H, d, J=7.3 Hz), 5.74 (1H, d, J=7.4 Hz), 4.43 (1H, t, J=7.9 Hz), 3.96 (1H, d, J=10.2 Hz), 3.87-3.78 (3H, m), 1.50-1.38 (1H, m), 1.29-1.22 (2H, m), 1.02 (14H, s), 0.86 (6H, d, J=6.4), 0.69-0.62 (2H, m); FAB-LRMS m/z 437 (MH$^+$). Anal. Calcd for C$_{21}$H$_{36}$N$_4$O$_4$Si: C, 57.77; H, 8.31; N, 12.83. Found: C, 57.79; H, 8.29; N, 12.83.

EXAMPLE 55

5'-O-(n-Butyldiisopropylsilyl)-2'-cyano-2'-deoxy-1-β-D-arabinofuranosylcytosine (55)

Compound 47a (500 mg, 2.90 mmol) was dissolved in dichloromethane (5.8 mL). N-Bromosuccinimide (463 mg, 2.60 mmol) was added thereto at 0° C., and the resultant mixture was stirred at room temperature for 2 hours. After the solvent was removed under reduced pressure, the residue was dissolved in DMF (2.5 mL), and CNDAC hydrochloride (500 mg, 1.73 mmol) and imidazole (531 mg, 7.80 mmol) were added thereto, followed by stirring at room temperature overnight. The reaction mixture was partitioned between ethyl acetate and water. The formed organic layer was washed with saturated brine, and the thus-washed organic layer was dried over sodium sulfate anhydrate. After removal of solvent, the residue was purified through silica gel column chromatography (0 to 9% methanol/chloroform), whereby the Compound 55 was obtained as a white foam (351 mg, 48%).

$^1$H-NMR (DMSO-$d_6$) δ 7.76 (1H, d, J=7.4 Hz), 7.26 (2H, br d), 6.26 (1H, d, J=5.9 Hz), 6.21 (1H, d, J=7.3 Hz), 5.73 (1H, d, J=7.4 Hz), 4.46-4.38 (1H, m), 3.95 (1H, d, J=9.6 Hz), 3.86-3.74 (3H, m), 1.36-1.30 (4H, m), 1.01 (14H, s), 0.86-0.83 (3H, m), 0.69-0.63 (2H, m); FAB-LRMS m/z 423 (MH$^+$). Anal. Calcd for $C_{20}H_{34}N_4O_4Si$: C, 56.84; H, 8.11; N, 13.26. Found: C, 56.10; H, 8.74; N, 12.89.

EXAMPLE 56

5'-O-[(3-Methylbutyl)diisopropylsilyl]-2'-cyano-2'-deoxy-1-β-D-arabinofuranosylcytosine (56)

The procedure of synthesizing Compound 55 was repeated, except that CNDAC hydrochloride (491 mg, 1.70 mmol) and Compound 53a (541 mg, 2.90 mmol) were employed, whereby the Compound 56 was obtained as a white foam (379 mg, 51%).

$^1$H-NMR (DMSO-$d_6$) δ 7.76 (1H, d, J=7.4 Hz), 7.28 (2H, br d), 6.25 (1H, d, J=7.3 Hz), 5.74 (1H, d, J=7.4 Hz), 4.43 (1H, t, J=7.9 Hz), 3.96 (1H, d, J=10.2 Hz), 3.87-3.78 (3H, m), 1.50-1.38 (1H, m), 1.29-1.22 (2H, m), 1.02 (14H, s), 0.86 (6H, d, J=6.4), 0.69-0.62 (2H, m); FAB-LRMS m/z 437 (MH$^+$). Anal. Calcd for $C_{21}H_{36}N_4O_4Si$: C, 57.77; H, 8.31; N, 12.83. Found: C, 57.38; H, 8.21; N, 12.68.

EXAMPLE 57

(2-Ethylbutyl)dicyclopropylsilane (57a)

Magnesium (2.43 g, 100 mmol) and iodine (catalytic amount) were added to THF (100 mL), and 1-bromo-2-ethylbutane (13.8 mL, 100 mmol) was added dropwise thereto in a nitrogen atmosphere for 20 minutes, followed by stirring at room temperature for 1 hour. After termination of exothermic reaction, the resultant mixture was further stirred at 50° C. for 5 hours, to thereby prepare 2-ethylbutylmagnesium bromide THF solution. Trichlorosilane (2.52 mL, 25.0 mmol) was dissolved in THF (26 mL), and cyclopropylmagnesium bromide THF solution (0.50M, 100 mL, 50 mmol) was added dropwise thereto in a nitrogen atmosphere at 0° C., followed by stirring at room temperature for 1 hour. Cuprous bromide (286 mg, 2.00 mmol) was added to the resultant mixture, and the above-prepared 2-ethylbutylmagnesium bromide THF solution (25.0 mL) was added dropwise thereto for 30 minutes, followed by stirring at 70° C. for 8 hours. The reaction mixture was left to cool, and saturated aqueous ammonium chloride and n-pentane were added thereto. The formed organic layer was washed three times with water and once with saturated brine, and the thus-washed organic layer was dried over sodium sulfate anhydrate. The solvent was removed, whereby the Compound 57a was obtained as a brown liquid (510 mg, 10%).

$^1$H-NMR (CDCl$_3$) δ 3.61-3.60 (1H, m), 1.38-1.30 (5H, m), 0.90-0.81 (6H, m), 0.65-0.60 (6H, m), 0.37-0.31 (4H, m), −0.45−−0.51 (2H, m).

5'-O-[(2-Ethylbutyl)dicyclopropylsilyl]-2'-cyano-2'-deoxy-1-β-D-arabinofuranosylcytosine (57)

The procedure of synthesizing Compound 55 was repeated, except that CNDAC hydrochloride (500 mg, 1.73 mmol) and Compound 57a (510 mg, 2.60 mmol) were employed, whereby the Compound 57 was obtained as a white foam (309 mg, 40%).

$^1$H-NMR (DMSO-$d_6$) 7.74 (1H, d, J=7.4 Hz), 7.28 (2H, br d), 6.25 (1H, d, J=5.9 Hz), 6.21 (1H, d, J=7.4 Hz), 5.77 (1H, d, J=7.4 Hz), 4.42-4.34 (1H, m), 3.99-3.77 (4H, m), 1.54-1.39 (1H, m), 1.36-1.29 (4H, m), 0.85-0.80 (6H, m), 0.60-0.50 (6H, m), 0.40-0.32 (4H, m), −0.38−−0.46 (2H, m); FAB-LRMS m/z 447 (MH$^+$).

EXAMPLE 58

Dicyclopropylisobutylsilane (58a)

Trichlorosilane (2.52 mL, 25.0 mmol) was dissolved in THF (26 mL), and cyclopropylmagnesium bromide THF solution (0.50M, 100 mL, 50 mmol) was added dropwise thereto in a nitrogen atmosphere at 0° C., followed by stirring at room temperature for 1 hour. Cuprous bromide (286 mg, 2.00 mmol) was added to the resultant mixture, and isobutylmagnesium bromide (1.00M, 25.0 mL, 25.0 mmol) was added dropwise thereto for 30 minutes, followed by stirring at 70° C. for 8 hours. The reaction mixture was left to cool, and saturated aqueous ammonium chloride and n-pentane were added thereto. The formed organic layer was washed three times with water and once with saturated brine, and the thus-washed organic layer was dried over sodium sulfate anhydrate. The solvent was removed, followed by purification through distillation under reduced pressure, whereby the Compound 58a was obtained as a colorless liquid (boiling point; 20 mmHg, 95 to 100° C. fraction, 1.46 g, 35%).

$^1$H-NMR (CDCl$_3$) δ 3.45 (1H, m), 1.91-1.86 (1H, m), 0.99-0.95 (6H, m), 0.63-0.57 (6H, m), 0.33-0.30 (4H, m), −0.43−−0.51 (2H, m).

5'-O-Dicyclopropylisobutylsilyl-2'-cyano-2'-deoxy-1-β-D-arabinofuranosylcytosine (58)

The procedure of synthesizing Compound 55 was repeated, except that CNDAC hydrochloride (500 mg, 1.73 mmol) and Compound 58a (438 mg, 2.60 mmol) were employed, whereby the Compound 58 was obtained as a white foam (247 mg, 34%).

$^1$H-NMR (DMSO-$d_6$) δ 7.75 (1H, d, J=7.4 Hz), 7.27 (2H, br d), 6.24 (1H, d, J=5.8 Hz), 6.20 (1H, d, J=7.6 Hz), 5.77 (1H, d, J=7.4 Hz), 4.41-4.34 (1H, m), 3.98-3.76 (4H, m), 1.93-1.81

(1H, m), 1.03-0.94 (6H, m), 0.60-0.50 (6H, m), 0.39-0.33 (4H, m), −0.36−-0.51 (2H, m); FAB-LRMS m/z 419 (MH$^+$).

EXAMPLE 59

[3-(tert-Butoxy)propyl]diisopropylsilane (59a)

The procedure of synthesizing Compound 51a was repeated, except that 1-bromo-3-(tert-butoxy)propane (5.40 g, 27.7 mmol) was employed, whereby the Compound 59a was obtained as a brown liquid (3.10 g, 49%).
$^1$H-NMR (CDCl$_3$) δ 3.44 (1H, br s), 1.58-1.53 (2H, m), 1.26 (9H, s), 1.10-0.96 (16H, m), 0.83-0.78 (2H, m).

5'-O-{[3-(tert-Butoxy)propyl]diisopropylsilyl}-2'-cyano-2'-deoxy-1-β-D-arabinofuranosylcytosine (59)

The procedure of synthesizing Compound 55 was repeated, except that CNDAC hydrochloride (1.11 g, 3.84 mmol) and Compound 59a (2.90 g, 12.6 mmol) were employed, whereby the Compound 59 was obtained as a white foam (425 mg, 23%).
$^1$H-NMR (CDCl$_3$) δ 7.86 (1H, d, J=7.4 Hz), 6.36 (1H, d, J=6.5 Hz) 5.81 (1H, d, J=7.4 Hz), 4.65 (1H, t, J=5.9 Hz), 4.10-3.93 (3H, m), 3.34-3.30 (1H, m), 1.66-1.58 (2H, m), 1.15 (9H, s), 1.06-1.04 (16H, m), 0.73-0.67 (2H, m); FAB-LRMS m/z 481 (MH$^+$).

EXAMPLE 60

Diisopropyl(3-methoxypropyl)silane (60a)

1-Bromo-3-methoxypropane (9.18 g, 60.0 mmol) was dissolved in THF (55 mL), and magnesium (1.53 g, 62.9 mmol) and iodine (catalytic amount) were added thereto, followed by stirring at room temperature for 20 minutes and at 55° C. for 5 minutes. The resultant mixture was added dropwise to diisopropylchlorosilane (8.88 mL, 52.0 mmol) in THF (65 mL) for 5 minutes, followed by stirring at room temperature for 1 hour. After termination of exothermic reaction, the resultant mixture was further stirred at 50° C. for 1.5 hours, and saturated aqueous ammonium chloride was added thereto. The resultant mixture was extracted with pentane, followed by washing with water six times and drying over sodium sulfate anhydrate. The solvent was removed under reduced pressure, whereby the Compound 60a was obtained as an yellow liquid (10.1 g, 89%).
$^1$H-NMR (CDCl$_3$) δ 3.44 (1H, br s), 3.35 (2H, t, J=6.6 Hz), 1.60-1.72 (2H, m), 0.97-1.03 (14H, m), 0.58-0.64 (2H, m).

5'-O-[Diisopropyl(3-methoxypropyl)silyl]-2'-cyano-2'-deoxy-1-β-D-arabinofuranosylcytosine (60)

Compound 60a (565 mg, 3.00 mmol) was dissolved in dichloromethane (6 mL), and N-bromosuccinimide (534 mg, 3.00 mmol) was added thereto at 0° C., and the resultant mixture was stirred at room temperature for 5 minutes. The solvent was removed under reduced pressure. The residue was dissolved in DMF (4.5 mL), and CNDAC hydrochloride (866 mg, 3.00 mmol) and imidazole (511 mg, 7.51 mmol) were added thereto, followed by stirring at room temperature for 1 hour. Methanol (0.1 mL) was added to the reaction mixture, and the resultant mixture was partitioned between ethyl acetate and water. The formed organic layer was washed with saturated brine, and the thus-washed organic layer was dried over sodium sulfate anhydrate. After removal of solvent, the residue was subjected to crystallization with t-butylmethyl ether, whereby the Compound 60 was obtained as a white powder (820 mg, 62%).
$^1$H-NMR (DMSO-d$_6$) δ 7.75 (1H, d, J=7.6 Hz), 7.27, 7.25 (each 1H, each br s), 6.25 (1H, d, J=5.9 Hz), 6.21 (1H, d, J=7.3 Hz), 5.73 (1H, d, J=7.6 Hz), 4.38-4.45 (1H, m), 3.76-3.97 (4H, m), 3.27 (2H, t, J=6.9 Hz), 3.20 (3H, s), 1.51-1.61 (2H, m), 1.01 (14H, s), 0.62-0.69 (2H, m).

EXAMPLE 61

(3-Ethoxypropyl)diisopropylsilane (61a)

1-Bromo-3-ethoxypropane (5.85 g, 35.0 mmol) was dissolved in THF (30 mL). Magnesium (900 mg, 37.0 mmol) and iodine (catalytic amount) were added thereto, and the resultant mixture was stirred at room temperature for 30 minutes and at 60° C. for 10 minutes. The resultant mixture was added dropwise to diisopropylchlorosilane (5.12 mL, 30.0 mmol) in THF (40 mL), followed by stirring at room temperature for 15 minutes and at 60° C. for 1.5 hours. Saturated aqueous ammonium chloride was added thereto, and the resultant mixture was extracted with pentane, followed by washing with water six times and drying over sodium sulfate anhydrate. The solvent was removed under reduced pressure, whereby the Compound 61a was obtained as an yellow liquid (6.52 g, 92%).
$^1$H-NMR (CDCl$_3$) δ 3.36-3.75 (5H, m), 1.61-1.72 (2H, m), 1.21 (3H, t, J=7.0 Hz), 0.97-1.03 (14H, m), 0.57-0.65 (2H, m).

5'-O-[(3-Ethoxypropyl)diisopropylsilyl]-2'-cyano-2'-deoxy-1-β-D-arabinofuranosylcytosine (61)

Compound 61a (809 mg, 4.00 mmol) was dissolve in dichloromethane (8 mL), and N-bromosuccinimide (712 mg, 4.00 mmol) was added thereto at 0° C., and the resultant mixture was stirred at room temperature for 10 minutes. The solvent was removed under reduced pressure. The residue was dissolved in DMF (4.5 mL), and CNDAC hydrochloride (1.26 g, 4.36 mmol) and imidazole (681 mg, 10.0 mmol) were added thereto, followed by stirring at room temperature for 3 hours. After methanol was added to the reaction mixture, the resultant mixture was partitioned between ethyl acetate and water. The formed organic layer was washed with saturated brine six times, and the thus-washed organic layer was dried over sodium sulfate anhydrate. After removal of solvent, the residue was subjected to crystallization with t-butylmethyl ether, whereby the Compound 61 was obtained as a white powder (1.10 g, 68%).
$^1$H-NMR (DMSO-d$_6$) δ 7.75 (1H, d, J=7.4 Hz), 7.27, 7.25 (each 1H, each br s), 6.21 (1H, d, J=5.9 Hz), 6.21 (1H, d, J=7.4 Hz), 5.73 (1H, d, J=7.4 Hz), 4.37-4.45 (1H, m), 3.76-3.98 (4H, m), 3.38 (2H, q, J=6.9 Hz), 1.50-1.61 (2H, m), 1.01 (14H, s), 0.62-0.68 (2H, m); FAB-LRMS (negative) m/z 451 (M-H)$^-$.

EXAMPLE 62

3'-O-[(3-Ethoxypropyl)diisopropylsilyl]-2'-cyano-2'-deoxy-1-β-D-arabinofuranosylcytosine (62)

Compound 61a (1.82 g, 8.99 mmol) was dissolved in dichloromethane (18 mL), and N-bromosuccinimide (1.60 g, 8.99 mmol) was added thereto at 0° C., and the resultant mixture was stirred at room temperature for 10 minutes. The solvent was removed under reduced pressure, and the residue was dissolved in DMF (5 mL). Subsequently, CNDAC hydrochloride (866 mg, 3.00 mmol) and imidazole (1.23 g, 18.1 mmol) were added thereto, and the resultant mixture was stirred at room temperature for 20 minutes and at 55° C. for 2 hours. After methanol was added to the reaction mixture, the resultant mixture was partitioned between ethyl acetate and water. The formed organic layer was washed with saturated brine six times, and the thus-washed organic layer was dried over sodium sulfate anhydrate. After removal of solvent, the residue was dissolved in methanol (5 mL), and methanesulfonic acid (0.33 mL, 4.5 mmol) was added thereto, followed by stirring at 0° C. for 30 minutes. Saturated aqueous sodium hydrogencarbonate and ethyl acetate were added to the reaction mixture, and the formed organic layer was washed with water and saturated brine, and the thus-washed organic layer was dried over sodium sulfate anhydrate. After removal of solvent, the residue was purified through neutral silica gel column chromatography (6% to 10% methanol/chloroform), whereby the Compound 62 was obtained as a white foam (310 mg, 23%).

$^1$H-NMR (DMSO-$d_6$) δ 7.79 (1H, d, J=7.6 Hz), 7.29, 7.24 (each 1H, each br s), 6.16 (1H, d, J=7.3 Hz), 5.77 (1H, d, J=7.6 Hz), 5.21 (1H, t, J=5.4 Hz), 4.63-4.66 (1H, m), 3.79-3.87 (2H, m), 3.56-3.77 (2H, m), 3.39 (2H, q, J=7.1 Hz), 1.52-1.60 (2H, m), 1.08 (3H, t, J=7.1 Hz), 1.01 (14H, s), 0.67-0.70 (2H, m); FAB-LRMS (negative) m/z 451 (M-H)$^-$.

EXAMPLE 63

5'-O-[tert-Butyldi(3-ethoxypropyl)silyl]-2'-cyano-2'-deoxy-1-β-D-arabinofuranosylcytosine (63)

Magnesium (330 mg, 13.5 mmol) and iodine (catalytic amount) were added to THF (13.5 mL), and in a nitrogen atmosphere 1-bromo-3-ethoxypropane (2.25 g, 13.5 mmol) was added dropwise thereto for 20 minutes, and the resultant mixture was stirring at room temperature for 1 hour. After termination of exothermic reaction, the resultant mixture was further stirred at 50° C. for 4 hours. In a nitrogen atmosphere, the resultant mixture was added dropwise to tert-butyldichlorosilane (1.06 g, 6.75 mmol) and cuprous bromide (20 mg, 0.14 mmol) in THF (6.75 mL) at 0° C., followed by stirring at 70° C. for 8 hours. The reaction mixture was left to cool, and saturated aqueous ammonium chloride and n-pentane were added thereto. The formed organic layer was washed three times with water and once with saturated brine, and the thus-washed organic layer was dried over sodium sulfate anhydrate. After removal of solvent, the resultant yellow liquid was dissolved in dichloromethane (7.4 mL), and N-bromosuccinimide (642 mg, 3.61 mmol) was added thereto at 0° C., and the resultant mixture was stirred at room temperature for 10 minutes. The solvent was removed under reduced pressure, and the residue was dissolved in DMF (3.3 mL), and CNDAC hydrochloride (530 mg, 1.85 mmol) and imidazole (378 mg, 5.55 mmol) were added thereto, followed by stirring at 60° C. overnight. Subsequently, methanol was added to the reaction mixture, and the resultant mixture was partitioned between ethyl acetate and water. The formed organic layer was washed with saturated brine, and the thus-washed organic layer was dried over sodium sulfate anhydrate. After removal of solvent, the residue was purified through neutral silica gel column chromatography (0% to 5% methanol/chloroform), whereby the Compound 63 was obtained as an yellow foam (310 mg, 23%).

$^1$H-NMR (DMSO-$d_6$) δ 7.71 (1H, d, J=7.6 Hz), 7.29, 7.25 (each 1H, each br s), 6.27 (1H, m), 6.20 (1H, d, J=7.6 Hz), 5.73 (1H, d, J=7.6 Hz), 4.38 (1H, m), 3.94 (1H, dd, J=2.2, J=11.7 Hz), 3.86-3.75 (3H, m), 3.37 (4H, q, J=7.1 Hz), 3.29 (2H, q, J=7.1 Hz), 3.16 (1H, d, J=5.4 Hz), 1.56 (4H, m), 1.07 (6H, t, J=7.1 Hz), 0.91 (9H, s), 0.63 (4H, m); FAB-LRMS m/z 509 (MH$^+$).

Each structural formula of Compounds 1 to 63 which are obtained in the above Examples was shown in Table 1 to 11.

TABLE 1

| Compound | Structural formula |
|---|---|
| 1 | (structure) |
| 2 | (structure) |
| 3 | (structure) |
| 4 | (structure) |

TABLE 1-continued
| Compound | Structural formula |
|---|---|
| 5 | 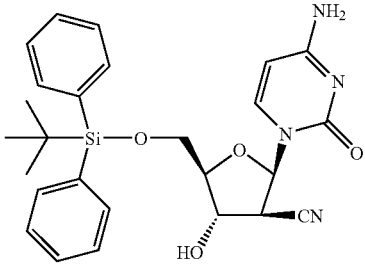 |
| 6 | 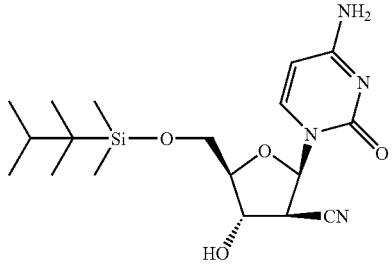 |
TABLE 2
| Compound | Structural formula |
|---|---|
| 7 | 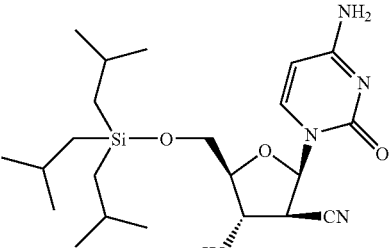 |
| 8 | 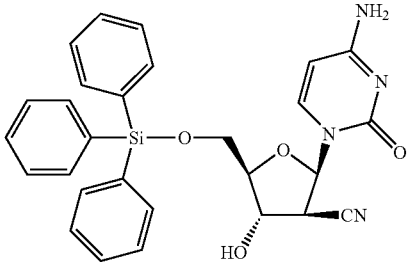 |
| 9 | 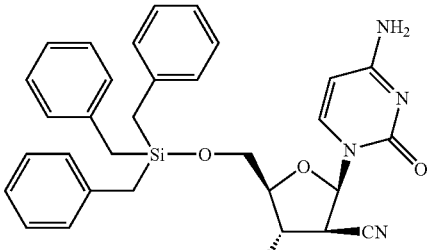 |
| 10 | 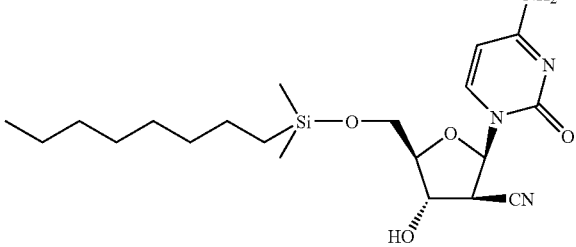 |

TABLE 2-continued

| Compound | Structural formula |
|---|---|
| 11 | |
| 12 | |

TABLE 3

| Compound | Structural formula |
|---|---|
| 13 | |
| 14 | |

TABLE 3-continued
| Compound | Structural formula |
|---|---|
| 15 | 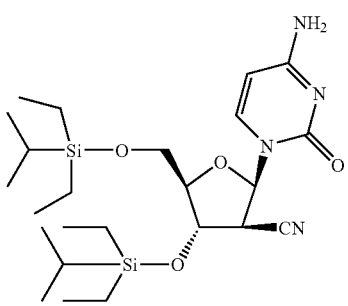 |
| 16 | 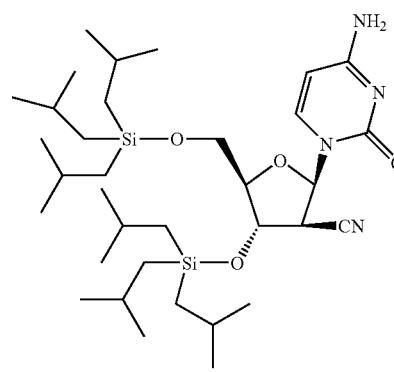 |
| 17 | 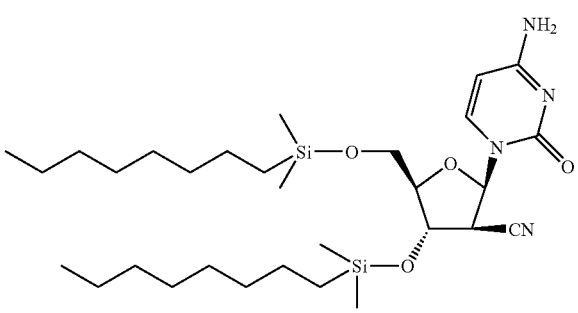 |
| 18 | 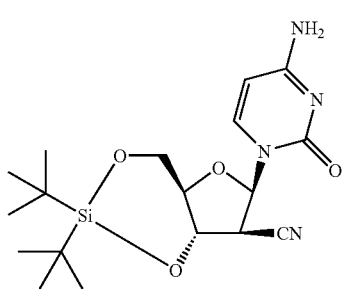 |

TABLE 4

| Compound | Structural formula |
|---|---|
| 19 | (cytidine derivative with 2'-CN, 3'-O-(dimethylthexylsilyl), 5'-OH) |
| 20 | (cytidine derivative with 2'-CN, 3'-O-(dimethylthexylsilyl), 5'-OH) · methanesulfonic acid |
| 21 | (cytidine derivative with 2'-CN, 3'-O-triethylsilyl, 5'-OH) |
| 22 | (cytidine derivative with 2'-CN, 3'-O-triisobutylsilyl, 5'-OH) |

TABLE 4-continued
| Compound | Structural formula |
|---|---|
| 23 | 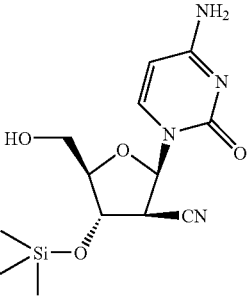 |
| 24 | 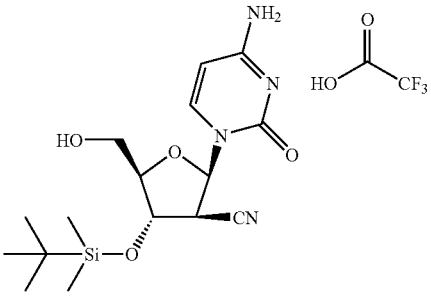 |
TABLE 5
| Compound | Structural formula |
|---|---|
| 25 | 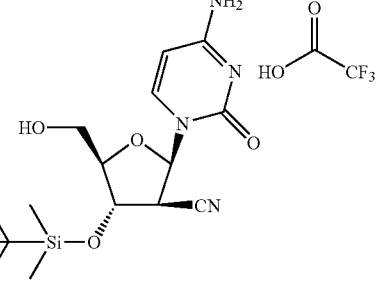 |
| 26 | 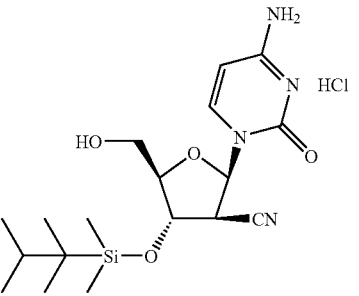 |
| 27 | 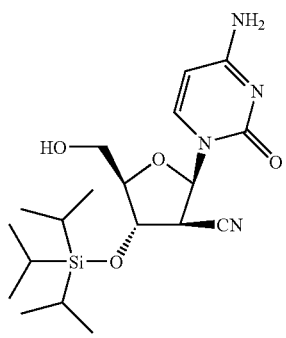 |
| 28 | 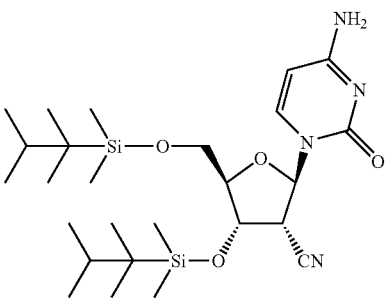 |

TABLE 5-continued

| Compound | Structural formula |
|---|---|
| 29 | |
| 30 | |

TABLE 6

| Example | Structural formula |
|---|---|
| 31 | |
| 32 | |

TABLE 6-continued

| Example | Structural formula |
|---|---|
| 33 | |
| 34 | |
| | |
| 35 | |
| 36 | |

TABLE 7

| Example | Structural formula |
|---------|-------------------|
| 37 | |
| 38 | |
| 39 | |
| 40 | |

TABLE 7-continued

| Example | Structural formula |
|---------|-------------------|
| 41 | |
| 42 | |

TABLE 8

| Example | Structural formula |
|---------|-------------------|
| 43 | |
| 44 | |

TABLE 8-continued
| Example | Structural formula |
|---|---|
| 45 | |
| 46 | |
| 47 | |
TABLE 9
| Example | Structural formula |
|---|---|
| 48 | |
TABLE 9-continued
| Example | Structural formula |
|---|---|
| 49 | |
| 50 | |
| 51 | |
| 52 | 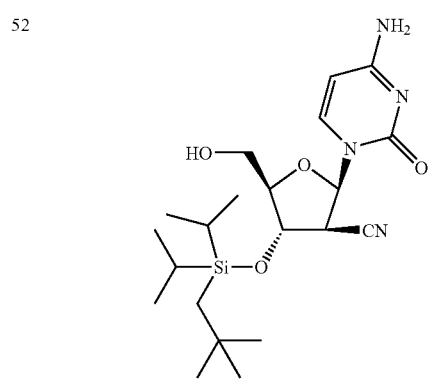 |

TABLE 9-continued
| Example | Structural formula |
|---|---|
| 53 | |
TABLE 10
| Example | Structural formula |
|---|---|
| 54 | |
| 55 | 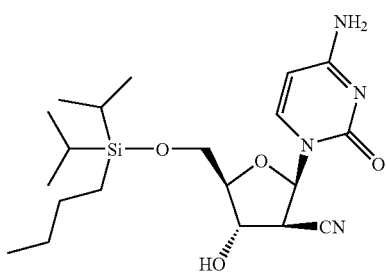 |
| 56 | 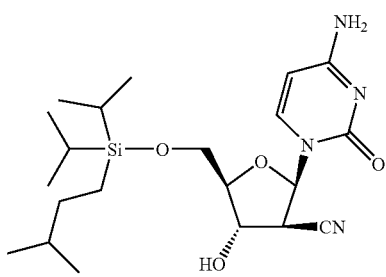 |
TABLE 10-continued
| Example | Structural formula |
|---|---|
| 57 | |
| 58 | 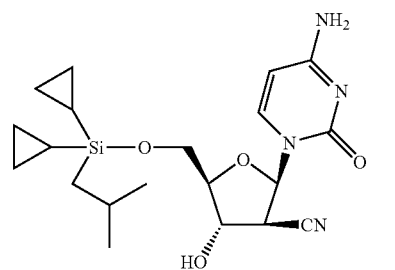 |
| 59 | 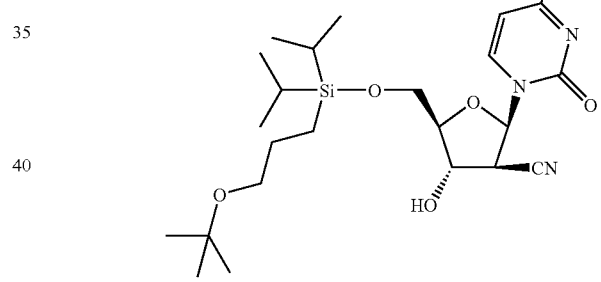 |
TABLE 11
| Example | Structural formula |
|---|---|
| 60 | 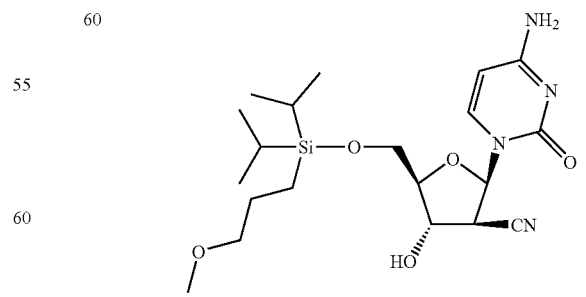 |

TABLE 11-continued

| Example | Structural formula |
|---|---|
| 61 | |
| 62 | |
| 63 | |

PHARMACOLOGICAL TEST EXAMPLE 1

Anti-Tumor Test Using Nude Mouse Subcutaneous Implantation System with Peroral Administration of CNDAC Compound Human large intestine cancer cell strain KM20C was subcutaneously subcultured in BALB/cA Jcl-nu mice (CLEA Japan, Inc.), and the resultant cancer tissues were cut into 2 mm dice fragments. Each of the fragments was subcutaneously implanted to a 6-week-old BALB/cA Jcl-nu mouse at the back thereof. On day 14 after the implantation, large and small diameters of the resultant tumor were measured, and the volume of the tumor was calculated by the following equation. The mice were grouped (6 animals per group) so that the groups were roughly equal in terms of average tumor volume.

$$Vt = \frac{1}{2}(Vl) \times (Vs)^2 \quad \text{(Equation 1)}$$

In the equation, Vt represents tumor volume, Vl represents large diameter of tumor, and Vs represents small diameter of tumor.

Each CNDAC compound was dissolved or suspended in 0.5% hydroxypropyl methyl cellulose solution which had been buffered with 100 mM citrate buffer (pH 6.0). From the next day after grouping, the mixture was perorally administered to each mouse once a day for consecutive 14 days in a dose which is equivalent, by mole, to 18 mg/kg/day of CNDAC.

On day 29 after the grouping, large and small diameters of the subcutaneously implanted tumor of each mouse were measured, and relative tumor volume (RTV) and inhibition rate (IR) were calculated by the following equations to evaluate anti-tumor effect of the compound. The test results are shown in Table 12.

$$RTV = Vt1/Vt2 \quad \text{(Equation 2)}$$

In the equation, RTV represents ratio of tumor volume, Vt1 represents tumor volume measured on the day of determination, and represents tumor volume measured on the day of grouping.

$$IR(\%) = [1-(RTVtest)/(RTVcont)] \times 100 \quad \text{(Equation 3)}$$

In the equation, IR represents tumor growth inhibition rate, RTVtest represents mean RTV value of a drug-administered group, and RTVcont represents mean RTV value of a non-treatment group.

TABLE 12

| Example No. | IR (%) |
|---|---|
| 1 | 75 |
| 2 | 65 |
| 3 | 82 |
| 6 | 82 |
| 7 | 79 |
| 10 | 68 |
| 18 | 69 |
| 19 | 89 |
| 21 | 85 |
| 24 | 83 |
| 27 | 85 |
| 31 | 89 |
| 32 | 85 |
| CNDAC | 46 |

As is shown in Table 12, the compounds of the present invention exhibit excellent anti-tumor effect as compared with CNDAC.

PHARMACOLOGICAL TEST EXAMPLE 2

Pharmacoliketics Test of CNDAC Compound in Donryu Rat

CNDAC compounds were perorally administered to Donryu rats (Charles River Laboratories Japan, Inc., 5 weeks old), and blood CNDAC level was measured. CNDAC compounds that have excellent absorbability upon peroral administration and are easily activated to CNDAC in an organism were selected on the basis of the blood CNDAC level.

Specifically, Donryu rats were fasted from the evening of the day before the test day. In the forenoon of the test day, each CNDAC compound (an amount equivalent, by mole, to 30 mg/kg of CNDAC) which had been dissolved or suspended in 0.5% hydroxypropyl methyl cellulose solution buffered with 100 mM citrate buffer (pH 5.0) was perorally administered, and blood was collected from the caudal vena cava at 15 and 30 minutes, and 1, 2, 4, and 8 hours after the administration, to thereby obtain serum samples (from 3 animals per time point). Compound and CNDAC levels of each serum sample were measured through HPLC. Area under concentration (AUC) of the blood CNDAC level from 0 to 8 hours was calculated, and bioavalability (BA), which indicates the amount of CNDAC released in the blood from the CNDAC compound, was determined from the following equation. The test results are shown in Table 13.

$$BA=[(AUCtest)/(AUCcont)]\times100(\%) \quad \text{(Equation 4)}$$

In the equation, BA represents bioavailability, AUCtest represents AUC of the blood CNDAC level upon peroral administration of CNDAC compound (in an amount equivalent to 30 mg/kg of CNDAC), and AUCcont represents AUC of the blood CNDAC level upon tail vein administration of CNDAC (in an amount equivalent to 30 mg/kg of CNDAC).

TABLE 13

| Example No. | BA (%) |
| --- | --- |
| 2 | 19.4 |
| 3 | 20.6 |
| 6 | 22.9 |
| 10 | 19.3 |
| 19 | 45.1 |
| 21 | 22.8 |
| 23 | 19.3 |
| 24 | 21.0 |
| 25 | 42.6 |
| 26 | 23.5 |
| 27 | 25.3 |
| 31 | 41.4 |
| 32 | 24.2 |
| CNDAC | 9.2 |
| P-CNDAC | 14.6 |

As is shown in Table 13, the compounds of the present invention exhibit excellent bioavailability as compared with a known CNDAC compound for peroral administration, P-CNDAC.

PHARMACOLOGICAL TEST EXAMPLE 3

Pharmacokinetics Test of CNDAC Compound in SD(IGS) Rat

CNDAC compounds were perorally administered to SD (IGS) rats (Charles River Laboratories Japan, Inc., 8 weeks old), and blood CNDAC level was measured. CNDAC compounds which have excellent absorbability upon peroral administration and are easily activated to CNDAC in an organism were selected based on the blood CNDAC level.

In the forenoon of the test day, each of CNDAC compounds (an amount equivalent, by mole, to 10 mg/kg of CNDAC) which had been dissolved or suspended in 0.5% hydroxypropyl methyl cellulose solution buffered with 100 mM citrate buffer (pH 5.0) was perorally administered, and blood was collected from the carotid artery at every point in time of 30 minutes and 1, 2, 4, 6, and 8 hours after the administration, to thereby obtain serum samples (from 2 to 3 animals per point). Compound and CNDAC levels in each serum sample were measured through LC/MS. Area under concentration (AUC) of the blood CNDAC level from 0 to 8 hours was calculated. The test results are shown in Table 14.

TABLE 14

| Example No. | AUC0-8 hr (ng · hr/mL) |
| --- | --- |
| 19 | 1163 |
| 45 | 1210 |
| CNDAC | 492 |
| P-CNDAC | 956 |

As is shown in Table 14, the compounds of the present invention exhibit a higher AUC as compared with a known CNDAC compound for peroral administration, P-CNDAC.

PHARMACOLOGICAL TEST EXAMPLE 4

Anti-Tumor Test Using Nude Mouse Subcutaneous Implantation System through Peroral Administration of CNDAC, P-CNDAC, or Compound 19 in an Equitoxic Dose Human large intestine cancer cell strain KM20C was subcutaneously subcultured in BALB/cA Jcl-nu mice (CLEA Japan, Inc.), and the resultant cancer tissues were cut into 2 mm dice fragments. Each of the fragments was subcutaneously implanted to a 6-week-old BALB/cA Jcl-nu mouse at the back thereof. On day 15 after the implantation, large and small diameters of the resultant tumor were measured, and the volume of the tumor was calculated through use of the following equation. The mice were grouped (6 animals per group) so that the average tumor volume was common to each group.

$$Vt=\frac{1}{2}(Vl)\times(Vs)^2 \quad \text{(Equation 5)}$$

In the equation, Vt represents tumor volume, Vl represents large diameter of tumor, and Vs represents small diameter of tumor.

CNDAC, P-CNDAC, or Compound 19 was dissolved or suspended in 0.5% hydroxypropyl methyl cellulose solution which had been buffered with 100 mM citrate buffer (pH 5.0). From the next day of grouping, the mixture was perorally administered to each mouse once a day for consecutive 14 days in an equitoxic dose.

Large and small diameters of the subcutaneously implanted tumor of each mouse were measured twice a week, and relative tumor volume (RTV) was calculated as an index indicating tumor growth through use of the following equations to evaluate anti-tumor effect of the compound. The test results are shown in FIG. 1.

$$RTV=Vt1/Vt2 \quad \text{(Equation 6)}$$

In the equation, RTV represents ratio of tumor volume, Vt1 represents tumor volume measured on the day of determination, and Vt2 represents tumor volume measured on the day of grouping.

As is shown in FIG. 1, an equitoxic dose of Compound 19 greatly reduces the tumor volume as compared with CNDAC and P-CNDAC. While CNDAC and P-CNDAC cause no deletion of tumor, Compound 19 deletes tumor in three cases in total six cases, revealing that the compound of the present invention exhibits excellent anti-tumor effect.

PREPARATION EXAMPLE 1 TABLETS

TABLE 15

| Compound 3 | 50 mg |
|---|---|
| Corn starch | 50 mg |
| Microcrystalline cellulose | 50 mg |
| Hydroxypropyl cellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

Tablets (250 mg/tablet) were prepared in the above formulation through a routine method.

PREPARATION EXAMPLE 2 GRANULES

TABLE 16

| Compound 19 | 300 mg |
|---|---|
| Lactose | 540 mg |
| Corn starch | 100 mg |
| Hydroxypropyl cellulose | 50 mg |
| Talc | 10 mg |

Granules (1,000 mg/sachet) were prepared in the above formulation through a routine method.

PREPARATION EXAMPLE 3 CAPSULES

TABLE 17

| Compound 20 | 100 mg |
|---|---|
| Lactose | 30 mg |
| Corn starch | 50 mg |
| Microcrystalline cellulose | 10 mg |
| Magnesium stearate | 3 mg |

Capsules (193 mg/capsule) were prepared in the above formulation through a routine method.

PREPARATION EXAMPLE 4 INJECTION

TABLE 18

| Compound 21 | 100 mg |
|---|---|
| Sodium chloride | 3.5 mg |
| Distilled water for injection | Appropriate amount (2 mL/ample) |

Injection was prepared in the above formulation through a routine method.

PREPARATION EXAMPLE 5 SYRUP

TABLE 19

| Compound 27 | 200 mg |
|---|---|
| Purified sucrose | 60 g |
| ethyl parahydroxybenzoate | 5 mg |

TABLE 19-continued

| butyl parahydroxybenzoate | 5 mg |
|---|---|
| flavor | Appropriate amount |
| Coloring agent | Appropriate amount |
| Purified water | Appropriate amount |

Syrup was prepared in the above formulation through a routine method.

PREPARATION EXAMPLE 6 SUPPOSITORIES

TABLE 20

| Compound 32 | 300 mg |
|---|---|
| Witepsol W-35 (registered trademark, a mixture of mono-, di-, and tri-glyceride of saturated fatty acids lauric acid to stearic acid, product of Dynamite Novel) | 1,400 mg |

Suppositories were prepared in the above formulation through a routine method.

The invention claimed is:

1. A pyrimidine nucleoside compound represented by the following formula (1):

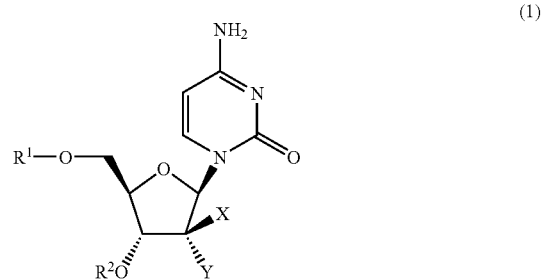

or a pharmaceutically acceptable salt thereof,
wherein
one of X and Y represents a cyano group, and the other represents a hydrogen atom;
one of $R^1$ and $R^2$ represents a hydrogen atom, a carbonyl group having a C1-C6 alkyl group which has been mono-substituted by an amino group, or a group represented by $(R^3)(R^4)(R^5)Si—$, and the other represents a group represented by $(R^6)(R^7)(R^8)Si—$, or $R^1$ and $R^2$ together form a 6-membered cyclic group represented by $—Si(R^9)(R^{10})—$;
$R^3$, $R^4$, $R^5$, $R^6$, $R^7$, and $R^8$ each represent a substituted or non-substituted C1-C10 linear or branched alkyl group, a substituted or non-substituted C3-C6 cycloalkyl group, a substituted or non-substituted C6-C14 aryl group, or a substituted C1-C6 alkyl group which has been substituted by one or two C6-C14 aryl groups, wherein the one or two C6-C14 aryl groups are optionally substituted by a substituent selected from the group consisting of a C1-C3 linear or branched alkyl group, a hydroxyl group, a C1-C6 linear or branched alkoxy group, an amino group, a halogen atom, a cyano group, and a nitro group; and R⁹ and R¹⁰ each represent a substituted or non-substituted C1-C6 linear or branched alkyl group.

2. The pyrimidine nucleoside compound of formula (1) or a pharmaceutically acceptable salt thereof according to claim 1, wherein
one of X and Y represents a cyano group, and the other represents a hydrogen atom;
one of $R^1$ and $R^2$ represents a hydrogen atom, a carbonyl group having a C1-C6 alkyl group which has been mono-substituted by an amino group, or a group represented by $(R^3)(R^4)(R^5)Si$—, and the other represents a group represented by $(R^6)(R^7)(R^8)Si$—, or $R^1$ and $R^2$ together form a 6-membered cyclic group represented by —Si$(R^9)(R^{10})$—;
$R^3$, $R^4$, $R^5$, $R^6$, $R^7$, and $R^8$, which may be identical to or different from one another, individually represent a C1-C8 linear or branched alkyl group optionally substituted with a substituent selected from the group consisting of a C1-C6 linear or branched alkoxy group, a C3-C6 cycloalkyl group, a phenyl group, and a benzyl group.

3. The pyrimidine nucleoside compound of formula (1) or a pharmaceutically acceptable salt thereof according to claim 1, wherein
one of X and Y represents a cyano group, and the other represents a hydrogen atom;
$R^1$ represents a hydrogen atom, a valyl group, or a group represented by $(R^3)(R^4)(R^5)Si$—;
$R^2$ represents a hydrogen atom or a group represented by $(R^6)(R^7)(R^8)Si$—, with the proviso that when $R^1$ is a hydrogen atom or a valyl group, $R^2$ does not represent a hydrogen atom; and
$R^3$, $R^4$, $R^5$, $R^6$, $R^7$, and $R^8$, which may be identical to or different from one another, each represent a C1-C8 linear or branched alkyl group or a C3-C6 cycloalkyl group.

4. The pyrimidine nucleoside compound of formula (1) or a pharmaceutically acceptable salt thereof according to claim 1, wherein
one of X and Y represents a cyano group, and the other represents a hydrogen atom;
$R^1$ represents a hydrogen atom, an L-valyl group, or a group represented by $(R^3)(R^4)(R^5)Si$—;
$R^2$ represents a hydrogen atom or a group represented by $(R^6)(R^7)(R^8)Si$—, with the proviso that when $R^1$ is a hydrogen atom or an L-valyl group, $R^2$ does not represent a hydrogen atom; and
any one of $R^3$, $R^4$, and $R^5$ and any one of $R^6$, $R^7$, and $R^8$, which may be identical to or different from each other, individually represent a C3-C8 linear or branched alkyl group or a cyclopropyl group, and the other groups, which may be identical to or different from each other, each represent a C1-C4 linear or branched alkyl group.

5. The pyrimidine nucleoside compound of formula (1) or a pharmaceutically acceptable salt thereof according to claim 1, wherein
one of X and Y represents a cyano group, and the other represents a hydrogen atom;
$R^1$ represents a hydrogen atom, an L-valyl group, a triisopropylsilyl group, a diethylisopropylsilyl group, a dimethylthexylsilyl group, or a dimethyl-n-octylsilyl group;
$R^2$ represents a hydrogen atom, a tert-butyldimethylsilyl group, a triisopropylsilyl group, a diethylisopropylsilyl group, a cyclopropyldiisopropylsilyl group, or a dimethylthexylsilyl group, with the proviso that when $R^1$ is a hydrogen atom or an L-valyl group, $R^2$ does not represent a hydrogen atom.

6. The pyrimidine nucleoside compound of formula (1) or a pharmaceutically acceptable salt thereof according to claim 1, which is selected from the group consisting of:
5'-O-triisopropylsilyl-2'-cyano-2'-deoxy-1-β-D-arabinofuranosylcytosine;
5'-O-diethylisopropylsilyl-2'-cyano-2'-deoxy-1-β-D-arabinofuranosylcytosine;
5'-O-dimethylthexylsilyl-2'-cyano-2'-deoxy-1-β-D-arabinofuranosylcytosine;
5'-O-(dimethyl-n-octylsilyl)-2'-cyano-2'-deoxy-1-β-D-arabinofuranosylcytosine;
3'-O-dimethylthexylsilyl-2'-cyano-2'-deoxy-1-β-D-arabinofuranosylcytosine;
3'-O-diethylisopropylsilyl-2'-cyano-2'-deoxy-1-β-D-arabinofuranosylcytosine;
3'-O-(tert-butyldimethylsilyl)-2'-cyano-2'-deoxy-1-β-D-arabinofuranosylcytosine;
3'-O-triisopropylsilyl-2'-cyano-2'-deoxy-1-β-D-arabinofuranosylcytosine;
3'-O-dimethylthexylsilyl-5'-O-(L-valyl)-2'-cyano-2'-deoxy-1-β-D-arabinofuranosylcytosine;
5'-O-(L-valyl)-3'-O-(tert-butyldimethylsilyl)-2'-cyano-2'-deoxy-1-β-D-arabinofuranosylcytosine; and
3'-O-cyclopropyldiisopropylsilyl-2'-cyano-2'-deoxy-1-β-D-arabinofuranosylcytosine.

7. The pyrimidine nucleoside compound of formula (1) or a pharmaceutically acceptable salt thereof according to claim 1, wherein the substituent(s) bonded to $R^3$, $R^4$, $R^5$, $R^6$, $R^7$, $R^8$, $R^9$ or $R^{10}$ is selected from the group consisting of a C1-C3 linear or branched alkyl group, a hydroxyl group, a C1-C6 linear or branched alkoxy group, an amino group, a halogen atom, a cyano group, and a nitro group.

8. A pharmaceutical composition comprising: a therapeutically effective amount of a pyrimidine nucleoside compound of formula (1) or a pharmaceutically acceptable salt thereof as recited in any of claims 1 to 6; and a pharmaceutically acceptable carrier.

9. A method for treating an intestinal tumor comprising administering to a subject in need thereof a therapeutically effective amount of a pyrimidine nucleoside compound of formula (1) or a pharmaceutically acceptable salt thereof as recited in any of claims 1 to 6.

* * * * *